(12) United States Patent
Zarembinski

(10) Patent No.: US 10,342,576 B2
(45) Date of Patent: Jul. 9, 2019

(54) INTEGRATED NEEDLE-CATHETER SYSTEMS AND METHODS OF USE

(71) Applicant: Christopher Zarembinski, Los Angeles, CA (US)

(72) Inventor: Christopher Zarembinski, Los Angeles, CA (US)

(*) Notice: Subject to any disclaimer, the term of this patent is extended or adjusted under 35 U.S.C. 154(b) by 0 days.

(21) Appl. No.: 15/294,575

(22) Filed: Oct. 14, 2016

(65) Prior Publication Data

US 2017/0135723 A1   May 18, 2017

Related U.S. Application Data

(60) Provisional application No. 62/256,037, filed on Nov. 16, 2015, provisional application No. 62/241,669, filed on Oct. 14, 2015.

(51) Int. Cl.
 *A61B 17/34* (2006.01)
 *A61B 34/20* (2016.01)
 (Continued)

(52) U.S. Cl.
 CPC ...... *A61B 17/3415* (2013.01); *A61B 17/3401* (2013.01); *A61B 17/3423* (2013.01); *A61B 17/3468* (2013.01); *A61B 17/3472* (2013.01); *A61B 34/20* (2016.02); *A61M 5/007* (2013.01); *A61M 25/0084* (2013.01); *A61M 25/1002* (2013.01); *A61B 17/3478* (2013.01);
 (Continued)

(58) Field of Classification Search
 CPC ...... A61B 17/3472; A61B 2018/00434; A61B 34/20; A61N 1/0551
 See application file for complete search history.

(56) References Cited

U.S. PATENT DOCUMENTS

| 5,830,189 A | 11/1998 | Chang |
| 6,572,593 B1 | 6/2003 | Daum |

(Continued)

FOREIGN PATENT DOCUMENTS

| WO | WO 2007/124260 | 11/2007 |
| WO | WO 2009/129460 | 10/2009 |
| WO | WO 2013/119258 | * 8/2013 |

OTHER PUBLICATIONS

Malec-Milewska, et al. The effectiveness of neurolytic block of sphenopalatine ganglion using zygomatic approach for the management of trigeminal neuropathy. Neurologia { Neurochirurgia Polska 49(2015) 389-394.*

(Continued)

*Primary Examiner* — Deanna K Hall
(74) *Attorney, Agent, or Firm* — Knobbe, Martens, Olson & Bear LLP

(57) ABSTRACT

In some embodiments, disclosed herein are systems and methods of treating a patient that can include the steps of accessing the sphenopalatine fossa, and cannulating the inferior orbital fissure from the sphenopalatine fossa to access the retro-orbital space. The sphenopalatine fossa can be accessed via various routes, including percutaneously. Accessing the sphenopalatine fossa can include the step of inserting a needle-catheter system into the sphenopalatine fossa. Integrated needle-catheter systems as described herein can also be configured to access the trigeminal ganglion, epidural space, intrathecal space, and other desired anatomical locations.

17 Claims, 36 Drawing Sheets

(51) Int. Cl.
  *A61M 5/00* (2006.01)
  *A61M 25/00* (2006.01)
  *A61M 25/10* (2013.01)
  *A61B 90/00* (2016.01)
  *A61B 18/14* (2006.01)
  *A61B 18/00* (2006.01)
  *A61N 1/05* (2006.01)
  *A61M 25/01* (2006.01)
  *A61M 25/06* (2006.01)
  *A61B 17/00* (2006.01)
  *A61N 7/02* (2006.01)
  *A61B 18/02* (2006.01)

(52) U.S. Cl.
  CPC .......... *A61B 18/02* (2013.01); *A61B 18/1492* (2013.01); *A61B 2017/003* (2013.01); *A61B 2018/00434* (2013.01); *A61B 2018/00577* (2013.01); *A61B 2034/2055* (2016.02); *A61B 2090/3966* (2016.02); *A61M 25/0147* (2013.01); *A61M 25/065* (2013.01); *A61N 1/0551* (2013.01); *A61N 7/02* (2013.01)

(56) References Cited

U.S. PATENT DOCUMENTS

| | | |
|---|---|---|
| 7,181,289 B2 | 2/2007 | Pflueger et al. |
| 7,580,753 B2 | 8/2009 | Kim et al. |
| 7,632,243 B2 | 12/2009 | Bialecki et al. |
| 8,088,119 B2 | 1/2012 | Saal et al. |
| 8,231,588 B2 | 7/2012 | Xia |
| 2004/0015068 A1 | 1/2004 | Shalev et al. |
| 2007/0021648 A1 | 1/2007 | Lenker et al. |
| 2010/0030187 A1 | 2/2010 | Xia |
| 2010/0057048 A1 | 3/2010 | Eldredge |
| 2011/0190662 A1 | 8/2011 | McWeeney |
| 2011/0276056 A1 | 11/2011 | Grigsby et al. |

OTHER PUBLICATIONS

Hajioff, Daniel, et al. "Precise cannulation of the foramen ovale in trigeminal neuralgia complicating osteogenesis imperfecta with basilar invagination: technical case report." Neurosurgery 46.4 (2000): 1005-1008.

International Search Report and Written Opinion in PCT Application No. PCT/US2016/057157 dated Jan. 26, 2017 in 9 pages.

\* cited by examiner

SECTION A-A

SECTION B-B

INTEGRATED NEEDLE-CATHETER SYSTEMS AND METHODS OF USE

REFERENCE TO RELATED APPLICATIONS

This application claims the benefit under 35 U.S.C. § 119(e) as a nonprovisional application of U.S. Prov. Pat. App. No. 62/241,669 filed on Oct. 14, 2015 and U.S. Prov. Pat. App. No. 62/256,037 filed on Nov. 16, 2015, both of which are hereby incorporated by reference in their entireties.

BACKGROUND

Field of the Invention

Disclosed herein are systems, devices, and methods for accessing various anatomical locations including the retro-orbital space, trigeminal ganglion, and the epidural space.

SUMMARY

Visualizing and treating intra-orbital conditions can be challenging, especially in the back of the eye. Current approaches for access to the retro-orbital space include incisions at the superior edge of the eye or sinonasal approaches. Conventional surgical access to the retro-orbital space requires bone resection with either a nasal or periorbital approach, which carries an increased risk of complications, morbidity, and mortality. As such, less invasive systems and methods for accessing the retro-orbital space are needed, and are described herein. In some embodiments, systems and methods for accessing the trigeminal ganglion, epidural space, and other anatomical locations are also described herein.

Catheterization of the retro-orbital space via the inferior orbital fissure offers a minimally invasive approach that does not necessarily require bone resection. Catheterization can be accomplished in some cases with a needle-catheter system configured to allow for allows a rapid cannulation of the retro-orbital space for a variety of diagnostic and therapeutic indications, including but not limited to delivery of small molecule, biologic, or therapeutic cell-based solutions; drainage of blood or abscesses; and electrical stimulation for treatment of disconjugate gaze or vision itself by stimulation of the optic nerve. The system can offer greater precision of catheterization through a locking mechanism and fully contained needle-catheter system. The catheter can be housed completely within the needle's hub with capability of being locked in place for stability of placement.

In some embodiments, disclosed herein is a method of treating a patient, that can include the steps of accessing the sphenopalatine fossa, and cannulating the inferior orbital fissure from the sphenopalatine fossa to access the retro-orbital space. The sphenopalatine fossa can be accessed via various routes, including percutaneously. Accessing the sphenopalatine fossa can include the step of inserting a needle into the sphenopalatine fossa. This can be accomplished via various approaches, including inserting the needle percutaneously proximate the coronoid process of the mandible; and redirecting the needle to the superior aspect of the sphenopalatine fossa. In other cases, accessing the sphenopalatine fossa can include the step of inserting a needle percutaneously inferior to the zygomatic arch to contact the lateral pterygoid plate; and redirecting the needle to the superior aspect of the sphenopalatine fossa. The methods can be performed under an imaging modality such as fluoroscopy. Cannulating the inferior orbital fissure can include the steps of inserting a catheter into the medial or lateral portions of the inferior orbital fissure, although the medial portion can be preferred in some embodiments. Cannulating the inferior orbital fissure can involve inserting a catheter that extends distally from an exit port of a needle positioned in the sphenopalatine fossa through the inferior orbital fissure. The catheter can be inserted at an angle to the longitudinal axis of the needle, such as about 10 degrees, 15 degrees, or 20 degrees in some embodiments. The catheter can be inserted a distance from about 2 cm to about 4 cm beyond the exit port of the needle in some cases. The catheter can be locked to the needle to prevent relative axial movement of the catheter with respect to the needle, and then the catheter can be later unlocked to allow relative axial movement of the catheter with respect to the needle. Following deployment of the catheter, contrast media can be injected into the retro-orbital space, and the retro-orbital space can be visualized via an imaging modality. One, two, or more therapeutic agents can be delivered to the retro-orbital space. The therapeutic agent can include, for example, a drug such as a steroid, an antibiotic, or a local anesthetic among others; a therapeutic cell (e.g., a stem cell, a progenitor cell, a fully differentiated cell, and/or a genetically engineered cell), and a blood product or derivative thereof such as, for example, platelet-rich plasma. The catheter can also be connected to suction in order to at least partially draining a fluid or other material that is present within the retro-orbital space. The method can also involve electrically stimulating a nerve or muscle proximate the retro-orbital space or another location in the body.

In some embodiments, disclosed herein is a needle-catheter system for accessing the retro-orbital space. The system can include a needle comprising a proximal hub, a central lumen, and an elongate shaft portion. The shaft portion of the needle can include a proximal nondeflectable segment and a distal deflectable segment. The elongate shaft of the needle can be sized and configured to percutaneously access the sphenopalatine fossa. The catheter can have a proximal hub, a central lumen, and a shaft. The needle-catheter system can be movable from a first configuration in which the catheter shaft is housed within the central lumen of the needle to a second configuration in which the catheter shaft extends distally beyond a distal end of the needle such that a distal end of the catheter shaft is positioned in the retro-orbital space via the inferior orbital fissure when the distal end of the needle shaft is in the sphenopalatine fossa. The proximal hub of the needle and the proximal hub of the catheter can include complementary threads configured to reversibly prevent relative movement between the needle and the catheter when the catheter is in the second configuration. In some embodiments, the axial length of the needle shaft is between about 2 inches and about 4 inches, such as about 3 inches. The catheter can extend distally beyond the distal end of the needle by about 3 cm in the second configuration. The deflectable segment of the needle can be deflected at an angle to the longitudinal axis of the deflectable segment. In some embodiments, the angle can be between about 10 degrees and about 20 degrees. The proximal hub of the needle and/or the catheter can include grooves to facilitate gripping. The proximal hub of the needle and/or the catheter can have any appropriate cross-section, such as trapezoidal in some embodiments. The needle-catheter system can also include a removable stylet to protect the needle lumen during deployment. Other anatomical locations including but not limited to the trigeminal ganglion, epidural space, and intrathecal space can also be accessed using systems and methods disclosed herein.

In some embodiments, disclosed herein is a method of treating a patient, that can include accessing the foramen ovale proximate the coronoid process of the mandible; and cannulating the foramen ovale to access the trigeminal ganglion. The foramen ovale can be accessed lateral to the coronoid process, superior to the mandibular notch, and inferior to the zygomatic arch in some embodiments, e.g., within about 2 cm from the coronoid process. The method can also include advancing a catheter through foramen ovale into the trigeminal ganglion. In some embodiments, the method can also include inflating a balloon against a portion of the trigeminal ganglion. The method can also include comprising applying electromagnetic energy to a portion of the trigeminal ganglion, and/or injecting a chemical ablative agent into a portion of the trigeminal ganglion. Cannulating the foramen ovale can include advancing a catheter that extends distally from an exit port of a needle positioned proximate the foramen ovale, which can be at an angle to the longitudinal axis of the needle in some embodiments. The catheter can be advanced, in some cases, a distance from about 2 cm to about 4 cm beyond the exit port of the needle. The angle can be, for example, between about 10 degrees and about 20 degrees. The method can also include locking the catheter to the needle to prevent relative axial movement of the catheter with respect to the needle, and/or unlocking the catheter to the needle to allow relative axial movement of the catheter with respect to the needle.

Also disclosed herein is an integrated needle-catheter system for accessing the trigeminal ganglion or other target locations as disclosed herein, for example. The system can include a needle comprising a proximal hub, a central lumen, and an elongate shaft portion. The shaft portion of the needle can include a proximal nondeflectable segment and a distal deflectable segment. The elongate shaft of the needle can be sized and configured to percutaneously access the foramen ovale from an entry point proximate the coronoid process. The system can also include a catheter that can include a proximal hub, a central lumen, and a shaft. The needle-catheter system can be movable from a first configuration in which the catheter shaft is housed within the central lumen of the needle to a second configuration in which the catheter shaft extends distally beyond a distal end of the needle such that a distal end of the catheter shaft is positioned proximate the trigeminal ganglion via the inferior orbital foramen when the distal end of the needle shaft is in the foramen ovale. The proximal hub of the needle and the proximal hub of the catheter can include complementary threads configured to reversibly prevent relative movement between the needle and the catheter when the catheter is in the second configuration. The system can also, in some embodiments include an expandable balloon on the distal end of the catheter. The balloon can have, for example an expanded volume of about 1 cc, and be generally pear-shaped in some embodiments.

In some embodiments, disclosed herein is a method of treating a patient that includes accessing the epidural space or the interthecal space percutaneously via an integrated needle-catheter system comprising a catheter movable with respect to a catheter, wherein the catheter is non-removably attached to the needle. The method can also include locking the catheter to the needle to prevent relative axial movement of the catheter with respect to the needle. The method can also, in some cases, include unlocking the catheter to the needle to allow relative axial movement of the catheter with respect to the needle, and/or injecting a therapeutic agent into the epidural space. The therapeutic agent can include, for example, one or more of a local anesthetic, a steroid, a non-steroidal anti-inflammatory, and a narcotic.

In some aspects, disclosed herein is an integrated needle-catheter system for accessing the epidural space or other target locations as disclosed herein, for example. The system can include a needle comprising a proximal hub, a central lumen, and an elongate shaft portion. The shaft portion of the needle can include a proximal nondeflectable segment and a distal deflectable segment. The elongate shaft of the needle can be sized and configured to percutaneously access the epidural space. The catheter can include a proximal hub, a central lumen, and a shaft. The needle-catheter system can be movable from a first configuration in which the catheter shaft is housed within the central lumen of the needle to a second configuration in which the catheter shaft extends distally beyond a distal end of the needle such that a distal end of the catheter shaft is positioned in the epidural space when the distal end of the needle shaft is proximate the ligamentum flavum. In some embodiments, the proximal hub of the needle and the proximal hub of the catheter can include complementary threads configured to reversibly prevent relative movement between the needle and the catheter when the catheter is in the second configuration.

DETAILED DESCRIPTION

The eye sits in a fat-filled bony socket in the skull, known as the orbit. The orbit includes the eye itself, as well as additional structures such as the orbital and retrobulbar fascia, extraocular muscles, cranial nerves II, III, IV, V, and VI, blood vessels, fat, the lacrimal gland with its sac and nasolacrimal duct, the eyelids, medial and lateral palpebral ligaments, check ligaments, the suspensory ligament, septum, ciliary ganglion and short ciliary nerves.

Visualizing and treating intra-orbital conditions can be challenging, especially in the back of the eye. Current approaches for access to the retro-orbital space includes incisions at the superior edge of the eye or sinonasal approaches. Conventional surgical access to the retro-orbital space requires bone resection with either a nasal or periorbital approach, which carries an increased risk of complications, morbidity, and mortality. As such, less invasive systems and methods for accessing the retro-orbital space are needed, and are described herein.

Figure 1:
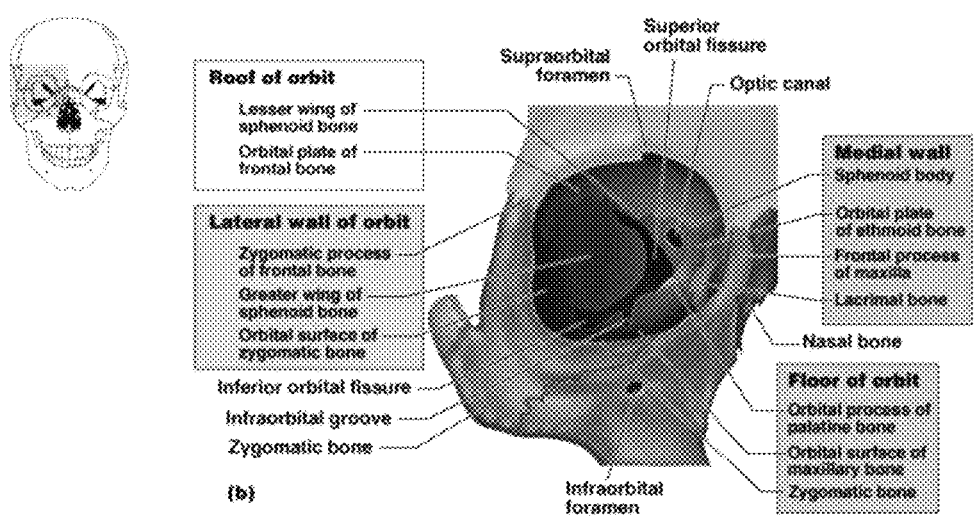
FIG. 1 illustrates an anterior view of selected bony anatomical features of the right orbit.

FIG. 1 illustrates an anterior view of selected bony anatomical features of the right orbit. The bony margins of the orbital canal are derived from the zygomatic bone laterally, the sphenoid bone, with its lesser wing forming the optic canal and its greater wing forming the lateral posterior portion of the bony orbital process, the maxillary bone inferiorly and medially which, along with the lacrimal and ethmoid bones, form the medial wall of the orbital canal. The ethmoid air cells are extremely thin, and form a structure known as the lamina papyracea, one of the most delicate bony structures in the skull. The lacrimal bone also contains the nasolacrimal duct. The superior margin and orbital rim, otherwise known as the orbital process, is formed by the frontal bone.

The roof (superior wall) of the orbit is formed primarily by the orbital plate frontal bone, and also the lesser wing of sphenoid near the apex of the orbit. The orbital surface presents medially by trochlear fovea and laterally by lacrimal fossa.

The floor (inferior wall) of the orbit is formed by the orbital surface of maxilla, the orbital surface of zygomatic bone and the minute orbital process of palatine bone. Medially, near the orbital margin, is located the groove for the nasolacrimal duct. Near the middle of the floor the infraorbital groove is present, which leads to the infraorbital foramen. The floor is separated from the lateral wall by the inferior orbital fissure, which connects the orbit to the sphenopalatine (also known as the pterygopalatine) and infratemporal fossa.

The medial wall of the orbit is formed primarily by the orbital plate of the ethmoid, as well as contributions from the frontal process of maxilla, the lacrimal bone, and a small part of the body of the sphenoid. It is the thinnest wall of the orbit, evidenced by pneumatized ethmoidal cells.

The lateral wall of the orbit is formed by the frontal process of zygomatic and more posteriorly by the orbital plate of the greater wing of sphenoid. The bones meet at the zygomaticosphenoid suture. The lateral wall is the thickest wall of the orbit.

The base of the orbit, which opens in the face, has four borders. The following bones take part in their formation: Superior margin: frontal bone and sphenoid; Inferior margin: maxilla, palatine and zygomatic; Medial margin: ethmoid, lacrimal bone, and frontal; and Lateral margin: zygomatic and sphenoid.

Figure 2:
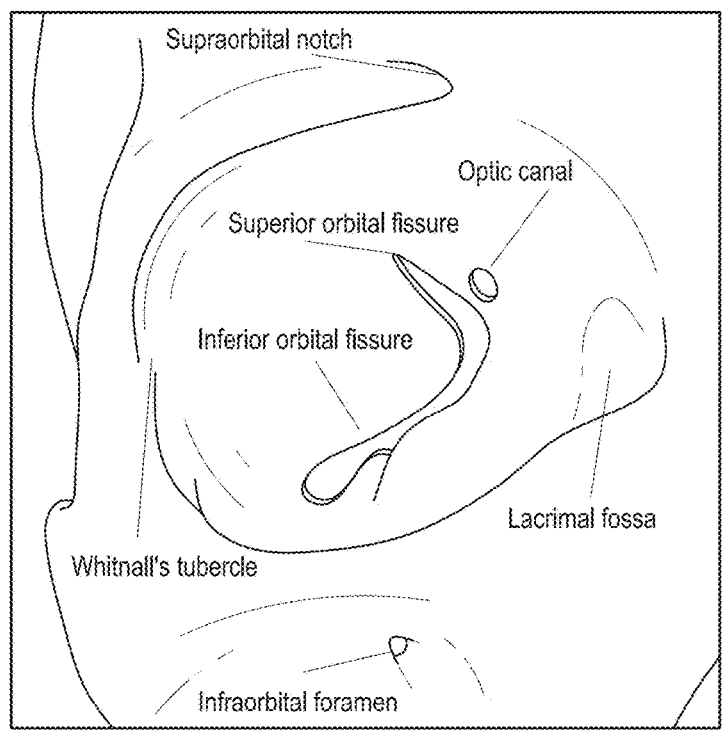
FIG. 2 illustrates a close-up view of selected anatomic features of the right orbit, including the superior and inferior orbital fissures.

As noted above, the sphenopalatine fossa is bounded by the maxilla anteriorly and the lateral pterygoid plate posteriorly and is readily anesthetized for treatment of facial pain or cluster headache (e.g., via a sphenopalatine ganglion block). The sphenopalatine fossa is in open communication with the floor of the orbit via the inferior orbital fissure (also illustrated in FIG. 2, along with the superior orbital fissure). As such, accessing the retro-orbital space through the sphenopalatine fossa, and then through the inferior orbital fissure would be highly advantageous in providing a minimally invasive access pathway (which does not require resection of bone) for a variety of diagnostic and therapeutic indications, including but not limited to delivery of therapeutic agents, drainage of blood and/or abscesses, electrical stimulation of the orbital contents for treating oculomotor abnormalities, and surgical access. To the inventors' knowledge, utilization of this natural anatomic pathway into the retro-orbital space for diagnostic and therapeutic purposes has not previously been described. Embodiments of such systems and methods will be described in detail herein.

Figure 3A:
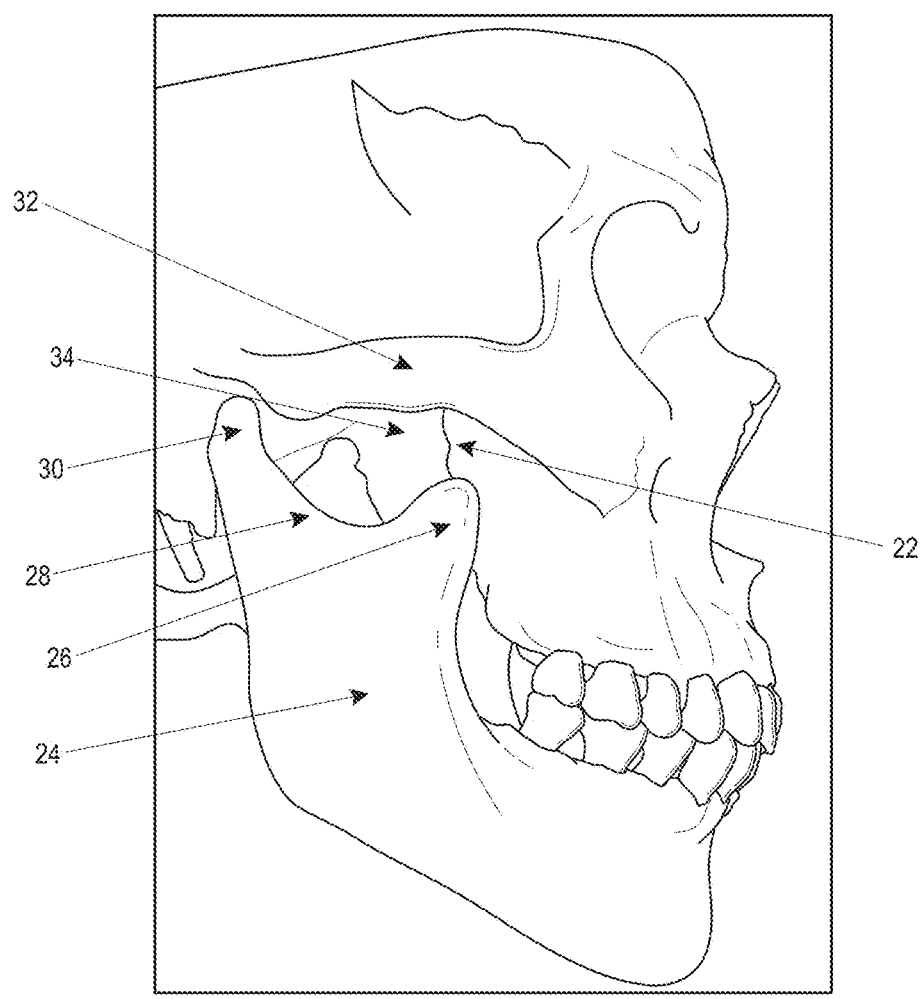
FIGS. 3A and 3B illustrate additional selected anatomical features relevant to systems and methods disclosed herein.
Figure 3B:
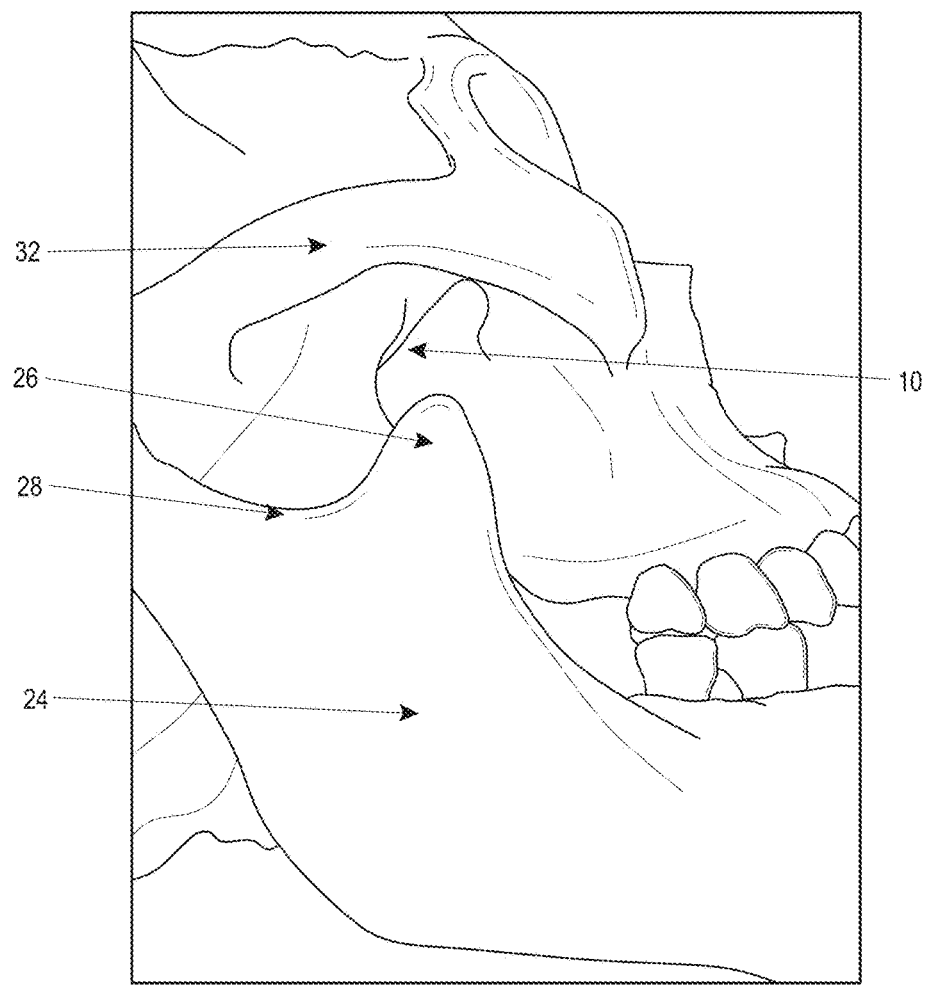
Figure 4A:
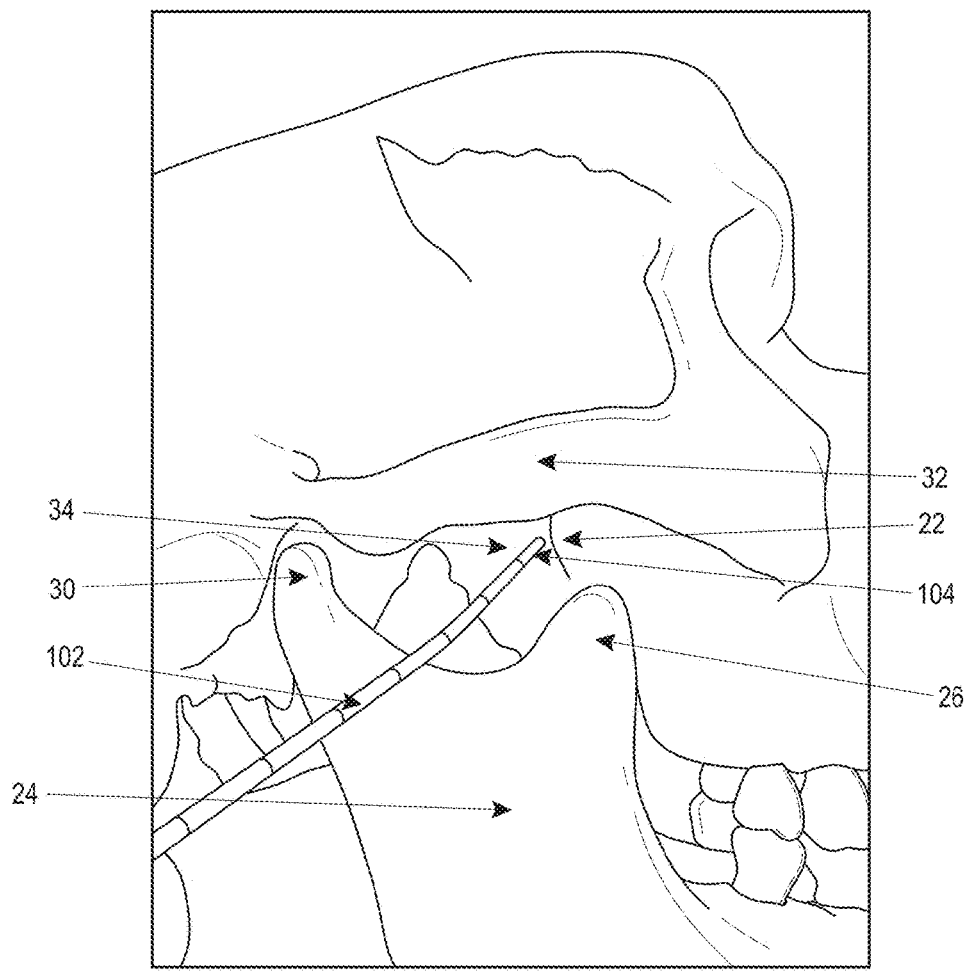
FIGS. 4A-5B illustrate a method of accessing the retro-orbital space from the sphenopalatine fossa via the inferior orbital foramen, according to some embodiments of the invention.
Figure 4B:
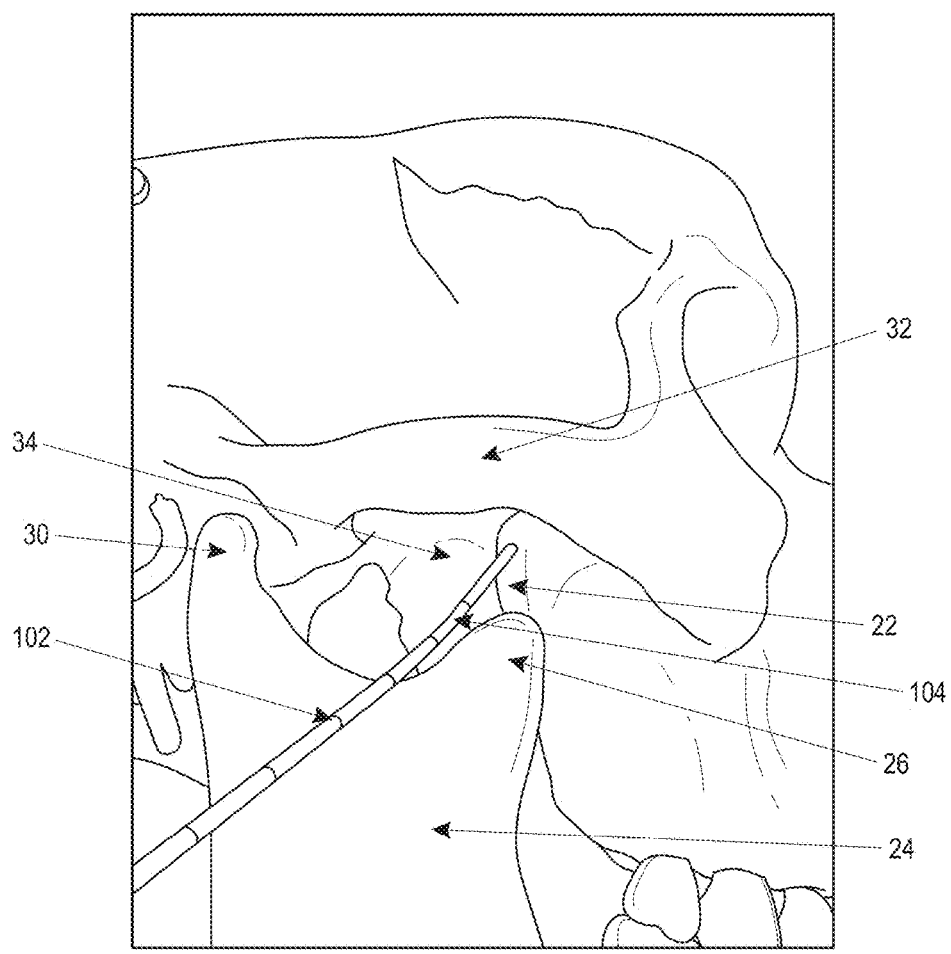
Figure 5A:
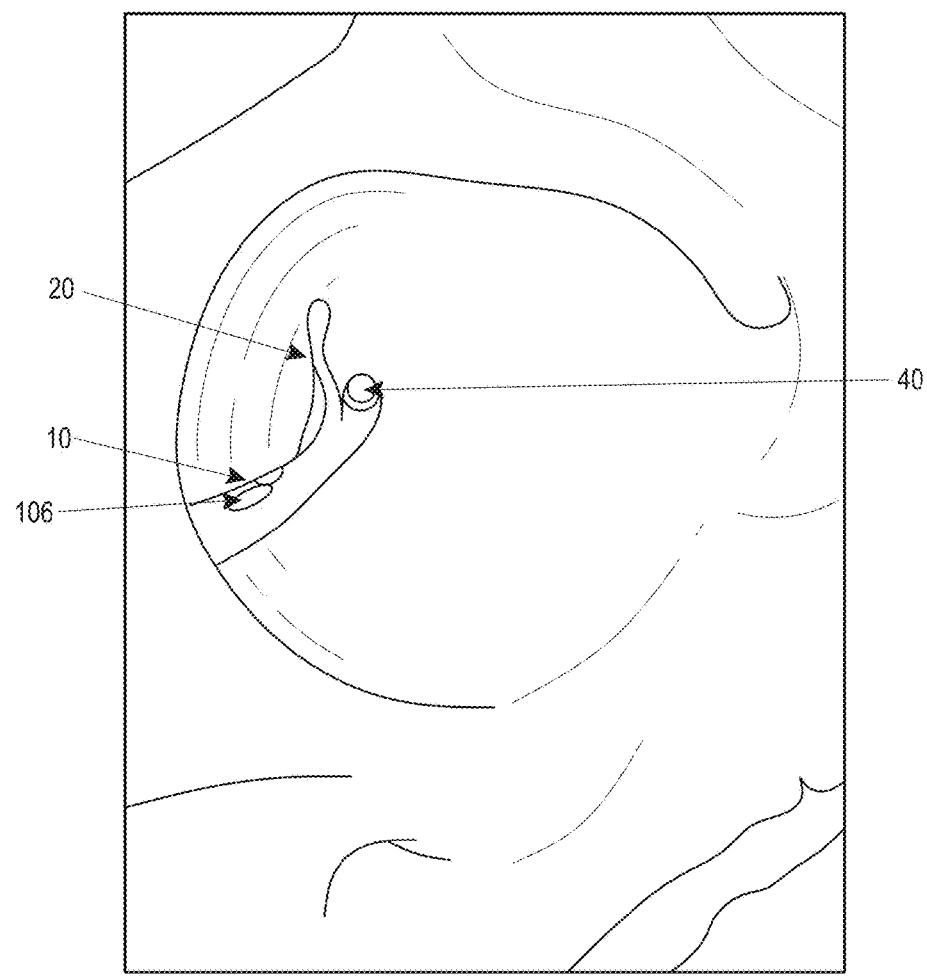
Figure 5B:
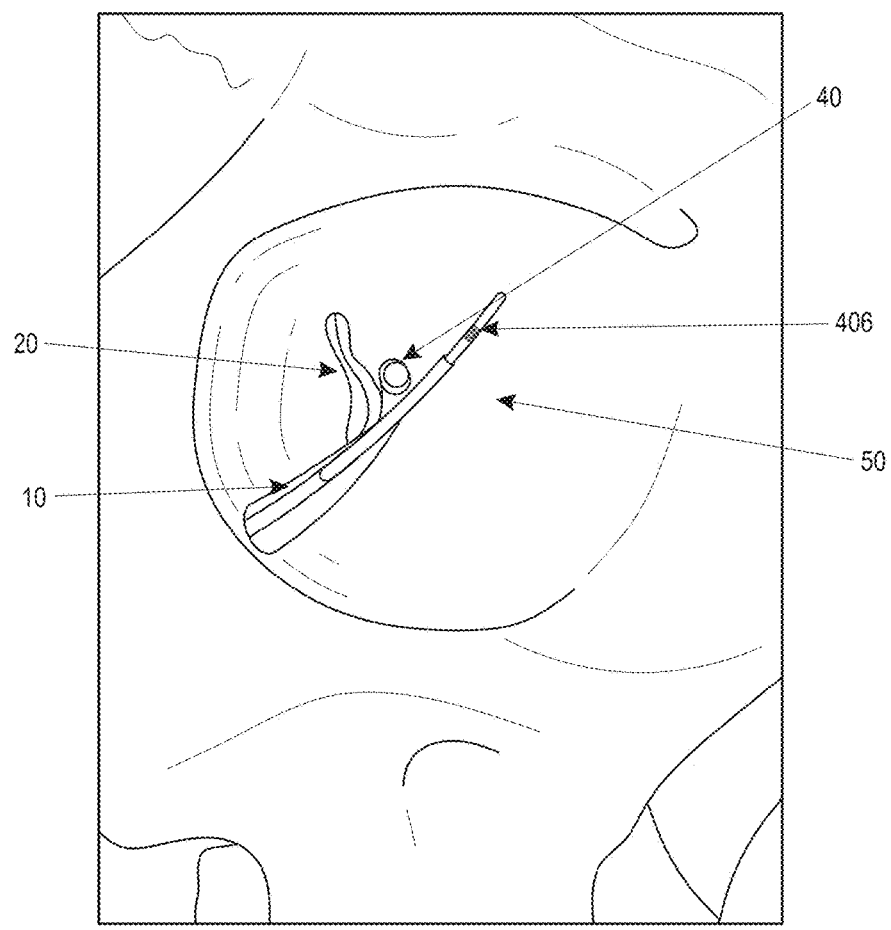

One non-limiting embodiment of accessing the retro-orbital space via the sphenopalatine fossa will now be described. FIG. 3A illustrates selected relevant anatomical landmarks of the right lateral side of the skull, including the sphenopalatine ganglion fossa 22, the lateral pterygoid plate 34, the head of the condylar process 30, the mandibular notch 28, and the coronoid process 26 of the mandible 24. Also illustrated is the zygomatic arch 32. FIG. 3B illustrates an angled view of FIG. 3A, in which the inferior orbital fissure 10 comes into view. Using standard sterile technique, an instrument such as the distal end 104 of a needle 102 of a needle-catheter system 100 can pierce skin of the face proximate the coronoid process 26 of the mandible 24 (and superior to the mandibular notch 28) in a first direction to contact the lateral pterygoid plate 34 in order to confirm depth of penetration, as illustrated in FIG. 4A. The distal end 104 of the needle 102 can then be redirected to the superior aspect of the sphenopalatine fossa 22 as illustrated in FIG. 4B. This can be performed under imaging, such as, for example, under fluoroscopic guidance on both AP and lateral fluoroscopic views. Once the needle 102 enters the sphenopalatine fossa 22, a second stage element, such as a catheter 106 for example can move distally out of a lumen of the first instrument, such as through a distally or laterally facing exit port of the needle 102, through the inferior orbital fissure 10, as illustrated in FIG. 5A. In some embodiments, the catheter 106 is advanced through the medial or lateral aspects of the inferior orbital fissure 10; the medial aspect may be preferred in some cases as discussed further below. Upon entry of the catheter 106 into the retro-orbital space 50 as illustrated in FIG. 5B (e.g., where the distal end of the catheter 106 extends 3 cm past the inferior orbital fissure 10 and into the retro-orbital space 50 in some cases), contrast medium can be injected to visualize the orbital contents further and document that no vascular penetration has occurred. The catheter position can then be adjusted depending on the desired clinical result.

Figure 6A:
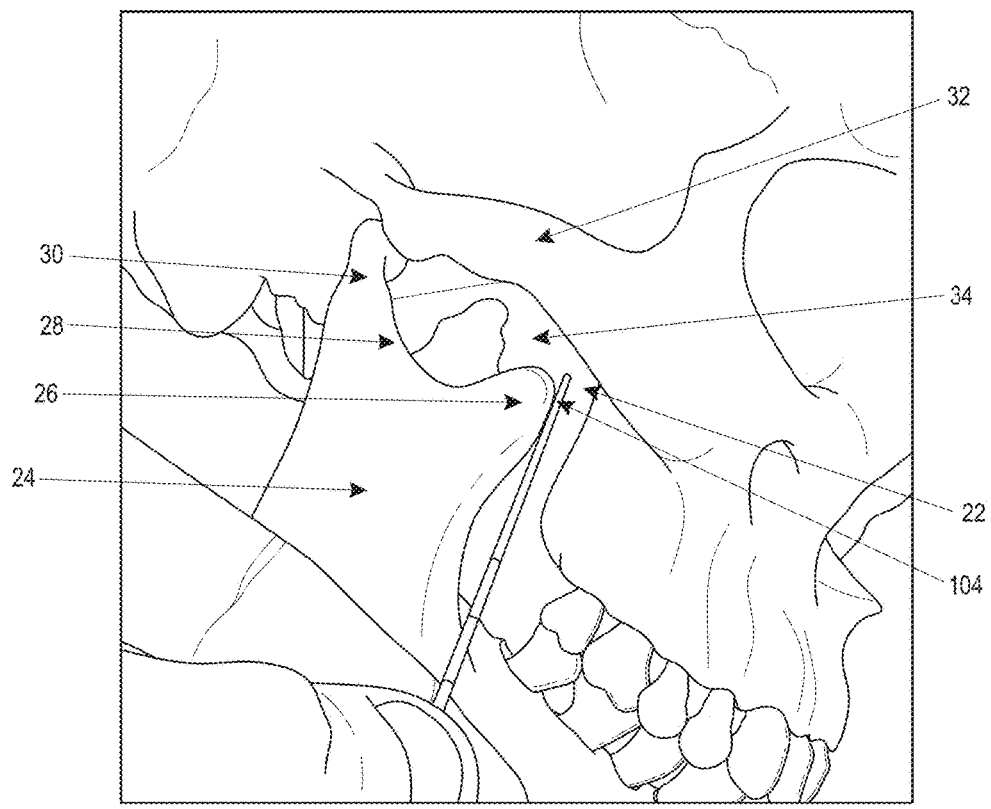
FIGS. 6A-6C illustrate another method of accessing the retro-orbital space from the sphenopalatine fossa via the inferior orbital foramen, according to some embodiments of the invention.
Figure 6B:
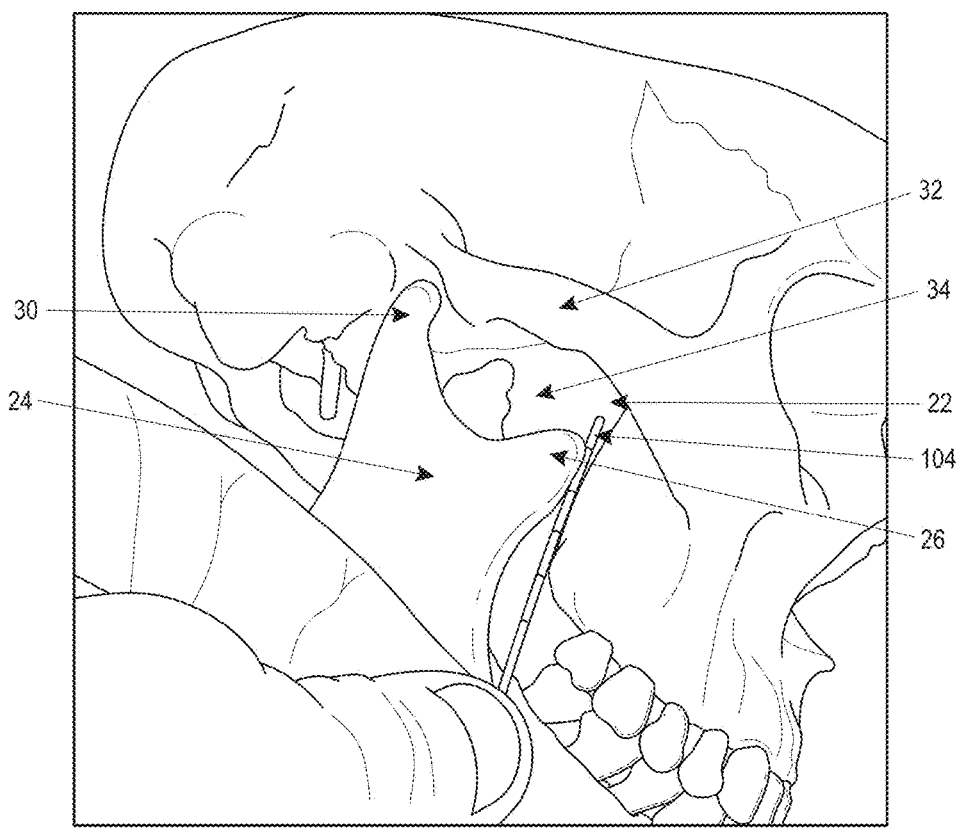
Figure 6C:
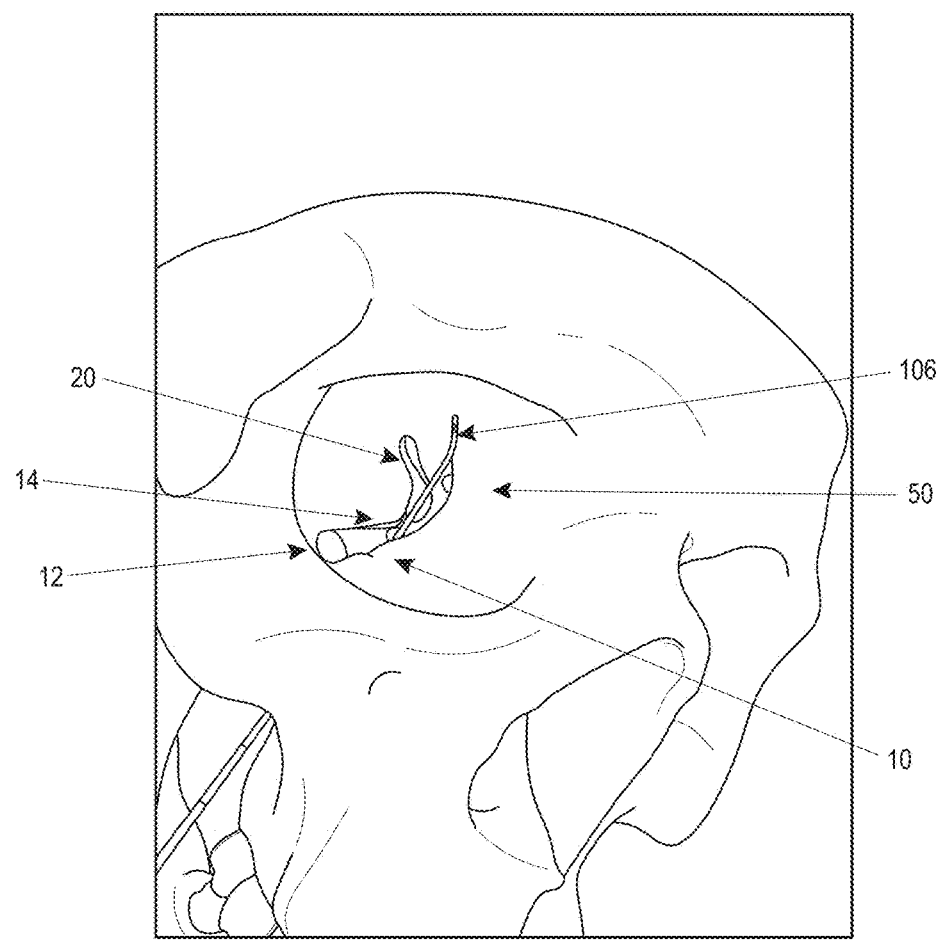

In other embodiments, the needle 102 can be percutaneously inserted directly in line or substantially in line with the sphenopalatine fossa 26 inferior to the zygomatic arch 32 and medial to the coronoid process 26 as illustrated in FIG. 6A. Contact with the lateral pterygoid plate 34 confirms depth of penetration and then the needle 102 is then redirected to the superior aspect of the sphenopalatine fossa 22 as illustrated in FIG. 6B followed by cannulation of the inferior orbital fissure 10 as described above. This approach leaves the catheter 106 in a relatively more mid-line position in the retro-orbital space 50 as illustrated in FIG. 6C. Although various approaches to the retro-orbital space via the sphenopalatine fossa 22 and the inferior orbital fissure 10 have been described herein, other approaches to access the retro-orbital space via the inferior orbital fissure 10 for example are also within the scope of the invention.

Figure 7:
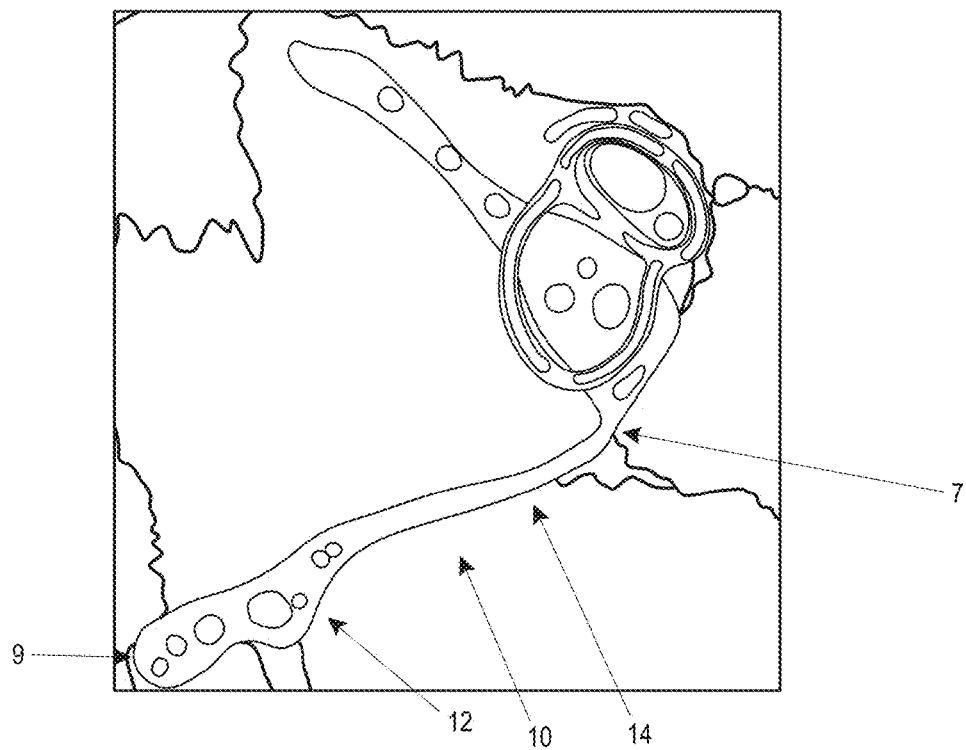
FIG. 7 illustrate the superior and inferior orbital fissures and selected related structures.

FIG. 7 illustrates the inferior orbital fissure 10, the superior orbital fissure 20, and structures that run within or proximate to the aforementioned fissures. The inferior orbital fissure 10 includes a lateral portion 12 and a medial portion 14. As shown, the lateral portion 12 of the inferior orbital fissure 10 includes several blood vessels and nerves running therethrough including the infraorbital artery, emissary veins, zygomatic and infra-orbital V2 branches of the trigeminal nerve, and the sensory root of pterygopalatine ganglion. Cannulation of the inferior orbital fissure 10 can potentially injure retro-orbital contents, as it may come into direct contact with neural structures, blood vessels, and the globe itself. In contrast, the medial portion 14 of the inferior orbital fissure has a relative paucity of blood vessels and nerves, and as such can be an advantageous and safe zone for cannulation from the sphenopalatine fossa. As such, in some embodiments, it is preferred that the medial portion 14 of the inferior orbital fissure 10 is cannulated. However, the lateral portion 12 of the inferior orbital fissure 10 can also be cannulated in some embodiments, such as a relatively medial zone of the lateral portion 12, for example. In some embodiments, the inferior orbital fissure 10 can be said to have a length running between its medial end 7 and the lateral end 9. In some embodiments, the inferior orbital fissure 10 is cannulated at a location along a section of the inferior orbital fissure 10 defined by about or no more than about the medial-most 80%, 75%, 70%, 65%, 60%, 55%, or 50% of its axial length in order to avoid or substantially avoid major neural structures and blood vessels within the inferior orbital fissure 10.

In some embodiments, systems and methods as disclosed herein can allow for a rapid cannulation of the retro-orbital space for a wide variety of indications. In some embodiments, one, two, or more therapeutic agents can be delivered to the retro-orbital space, such as via a lumen of the catheter. The therapeutic agent could be one, two, or more drugs, stem cells, progenitor cells, and/or other biological agents in some embodiments. In some embodiments, the drug could be a steroid, other anti-inflammatory agent, anti-angiogenesis agents, immunosuppressant, or biological mediator to treat, for example, an autoimmune condition such as, for example, Graves' ophthalmopathy, orbital pseudotumor, or optic neuritis. In some embodiments, the drug could be an antibiotic for treating an infection, such as orbital cellulitis, periorbital cellulitis, or an abscess for example. The drug could be in some cases, an anti-bacterial, anti-viral, anti-fungal, anti-parasitic, or any combination of the foregoing. In some embodiments, the therapeutic agent could be one or more chemotherapeutic agents to treat a benign or malignant tumor, or another cancer such as lymphoma for example. In some embodiments, the therapeutic agent could be an antibody, antigen, vaccine, and/or a blood-derived formulation such as, for example, a platelet-rich plasma formulation. In some embodiments, the therapeutic agent could include one, two, or more types of cells including stem or other therapeutic cells, progenitor cells, or a combination thereof. In some embodiments, the therapeutic agent could include adipose tissue, hyaluronic acid, or another filler for an aesthetic/reconstructive indication. In some embodiments, the therapeutic agent could be a growth factor or a growth factor inhibitor. In some embodiments, the therapeutic agent could be a viral vector, plasmid, or other vector, such as for gene therapy indications. Non-limiting specific examples of therapeutic agents that can be delivered using systems and methods herein include acyclovir, amikacin, anecortane acetate, anthracenedione, anthracycline, an azole, amphotericin B, bevacizumab, camptothecin, cefuroxime, chloramphenicol, chlorhexidine, chlorhexidine digluconate, clotrimazole, a cephalosporin, corticosteroids, dexamethasone, econazole, epipodophyllotoxin, fluconazole, flucytosine, fluoropyrimidines, fluoroquinolones, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymixin B, propamidine isethionate, pyrimidine nucleoside, ranibizumab, squalamine lactate, sulfonamides, triamcinolone, triamcinolone acetonide, triazoles, vancomycin, antivascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, ganciclovir, cidofovir, foscarnet, diclofenac, nepafenac, ketorolac, ibuprofen, indomethacin, fluorometholone, rimexolone, anecortave, cyclosporine, methotrexate, tacrolimus and combinations thereof. In some embodiments, a catheter or other delivery tool is positioned in the sphenopalatine fossa and/or the infraorbital fissure and the therapeutic agent is allowed to flow or otherwise travel into the retroorbital space across the inferior orbital fissure without a portion of the catheter or other delivery tool necessarily needing to be physically within the retroorbital space.

In some embodiments, the catheter can be connected to suction to drain material such as blood or pus, for example, or include a cutting element configured to drain an abscess, for example. In some embodiments, the distal end of the catheter can include or be operably associated with an energy delivery element to treat the retro-orbital space, including a surgical procedure or ablation of a tumor, as one example. In some embodiments, the catheter can be configured for RF ablation and include one, two, or more monopolar or bipolar RF electrodes or have a tip or other area(s) configured to ablate tissue (and/or create a non-ablative tissue effect) with other energy modalities. For example, other types of energy that can be used to ablate tissue include laser, ultrasound such as focused ultrasound or high intensity focused ultrasound (HIFU), microwave, infrared, visible, or ultraviolet light energy, electric field energy, magnetic field energy, cryoablation, combinations of the foregoing, or other modalities. For some forms of energy, the energy can be launched from a source carried by the distal end of the catheter, such as, for example, ultrasound transducers, microwave coil arrays, laser light sources, and others as will be understood in the art. For the same, or other energy forms, the energy source may be coupled to the proximal end of the catheter and the energy propagated distally through the catheter to an energy interface at the distal end of the catheter. Energy may be propagated along any appropriate conduit or circuit, such as fiber optics, conductive wires, one or more lumens (e.g., for cryogenic media) or others as appropriate for the energy source.

In some embodiments, the catheter can include or be configured to deliver one or more endoscopic cameras into the retro-orbital space for visualization and diagnostic purposes, or an imaging element such as, for example, an ultrasound probe.

In some embodiments, the catheter can deliver another medical device into the retro-orbital space intended for permanent or temporary implantation, including an implant such as a therapeutic agent delivery implant for example (including one, two, or more of the therapeutic agents described elsewhere herein), radioactive pellets, a sensor, a stent, a stimulation device such as an electrical stimulator, and the like. In some embodiments, the catheter can be configured for retrieval of a medical device including those mentioned herein.

In some embodiments, the catheter can include one or more electrodes, and be configured to stimulate one or more extraocular, intraocular, or other muscles or nerves proximate the retro-orbital space to treat disconjugate gaze for example, or even to stimulate the optic or other nerves to improve vision.

In some embodiments, systems and methods as disclosed herein can be utilized to cannulate the foramen ovale of the skull via a percutaneous route. The foramen ovale is a natural hole at the base of the skull, situated in the posterior part of the sphenoid bone, posterolateral to the foramen rotundum, and anteromedial to the foramen spinosum. In some individuals with anatomic variants, the foramen ovale actually is divided into 2, 3, or more component holes. The motor root of the trigeminal nerve, the mandibular nerve, the accessory meningeal artery, the lesser petrosal nerve (a branch of the glossopharyngeal nerve), an emissary vein connecting the cavernous sinus with the pterygoid venous plexus, and occasionally the anterior trunk of the middle meningeal vein pass through the foramen ovale.

Cannulation of the foramen ovale can be useful for various indications including but not limited to performing a balloon or other rhizotomy of the trigeminal ganglion for the treatment of trigeminal neuralgia. Trigeminal neuralgia is a neuropathic pain syndrome, described as sudden unilateral, severe brief, stabbing recurrent episodic pain within the distribution of the trigeminal nerve. Pain severity typically correlates with reduced daily functions and poor health status. There are generally two types: Type 1 is episodic and sharp; Type 2 is constant, dull and burning. The pathophysiology of trigeminal neuralgia is poorly understood, but may be related to ephaptic conduction caused by segmental demyelination and artificial synapse formation. Large diameter partially demyelinated A fibers conduct to small diameter poorly myelinated A-delta and unmyelinated nociceptive C fibers, which can result in paroxysmal facial pain. The superior cerebellar artery may cause vascular compression of the trigeminal nerve at the root entry zone. Other causes of demyelination may be due to tumor, plaque within brainstem in multiple sclerosis, aneurysm, AV malformation, and atherosclerosis. Trigeminal neuralgia is typically a clinical diagnosis based on symptoms, including a history of paroxysmal electric pain in trigeminal distribution on one side of the face. Trigger areas, when stimulated, also bring on the onset of pain. There are typically periods of remission and exacerbation, and can be more severe in the morning and absent during sleep. Physical exam is generally normal. Imaging studies such as MM can rule out other differential diagnoses such as tumors and multiple sclerosis.

First-line treatment for trigeminal neuralgia is typically medication management with membrane stabilizing medications, such as carbamazepine, oxcarbazepine, valproic acid, gabapentin, or pregabalin, for example. Microvascular decompression is an option if the patient is robust healthwise; rhizotomy including balloon, chemical, or electromagnetic energy (e.g., RF or gamma knife) rhizotomy in more elderly or debilitated patients. Balloon rhizotomy is a low cost, simple therapeutic modality. Percutaneous balloon rhizotomy selectively injures the myelin present in large myelinated fibers that mediate light touch. Balloon rhizotomy is generally selective for large fibers but not selective for pain, and preserves small unmyelinated fibers that mediate pain and temperature without injuring axons. Balloon rhizotomy thus reduces sensory neuronal input, thereby turning off the trigger for neuropathic trigeminal pain.

Figure 7A:
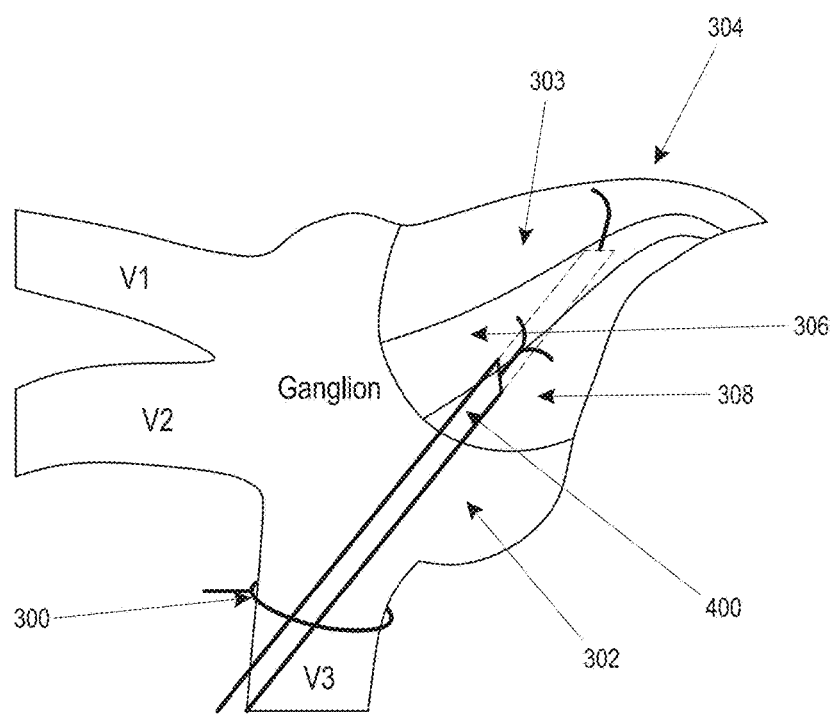
FIG. 7A schematically illustrates a catheter being placed into the foramen ovale and the trigeminal ganglion as well as the trigeminal root.

In a conventional balloon rhizotomy procedure, the patient is traditionally supine with fluoroscopic identification of the foramen ovale. A 14 gauge needle is passed about 6 cm towards the foramen ovale, starting intraorally adjacent to the corner of mouth. The balloon is then advanced to the intersection of the clivus and petrous ridge and inflated with about 1 ml slowly with water soluble contrast. After between about 1 minute and about 5 minutes, the balloon is deflated. The location in which the balloon is deployed matters in relation to the specific branch(es) of trigeminal nerve to be treated; precision control can be important. FIG. 7A schematically illustrates a catheter 400 being placed into the foramen ovale 300 and the trigeminal ganglion 302 as well as the trigeminal root 304 which encompasses the first 303, second 306, and third 308 divisions of the trigeminal nerve. In some embodiments, use of a pear-shaped balloon may improve outcome and corresponds to the inner anatomy of the Meckel cave—the distal protrusion surrounding the trigeminal ganglion 302 and the distal part of the trigeminal root 304. However, axially symmetric balloons can also be utilized in some embodiments. A pear-shaped balloon can have a distal zone with a first relatively narrower diameter, and a proximal zone with a second relatively wider narrower and a bulbous shape.

Typically, the average duration of benefit of a balloon rhizotomy is 2 years, with 15% recurrence of pain after 3 years. Type 1 trigeminal neuralgia may be associated with a better outcome. Post procedure numbness is a predictor of longer duration of analgesia and less recurrence. Complications associated with trigeminal rhizotomy include hypoesthesia, reported by almost all patients and usually transient. Anesthesia dolorosa is also possible. Rarely, masseter weakness, hearing loss, transient blindness, abducens weakness, loss of olfactory sense, changes in lacrimation, AV fistula, subarachnoid hemorrhage, meningitis, and loss of corneal reflexes can be seen.

Figure 7B:
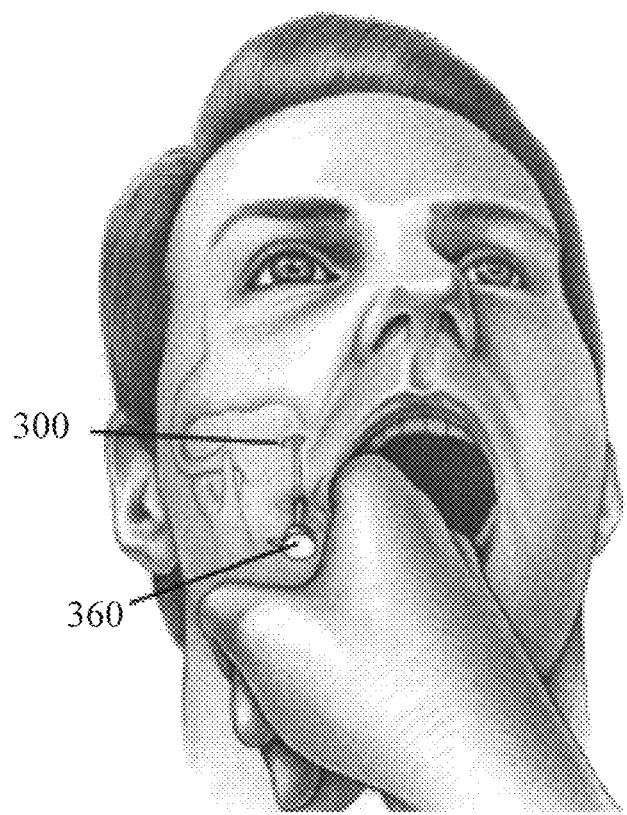
FIGS. 7B-7C illustrates a traditional approach to a trigeminal rhizotomy procedure.
Figure 7C:
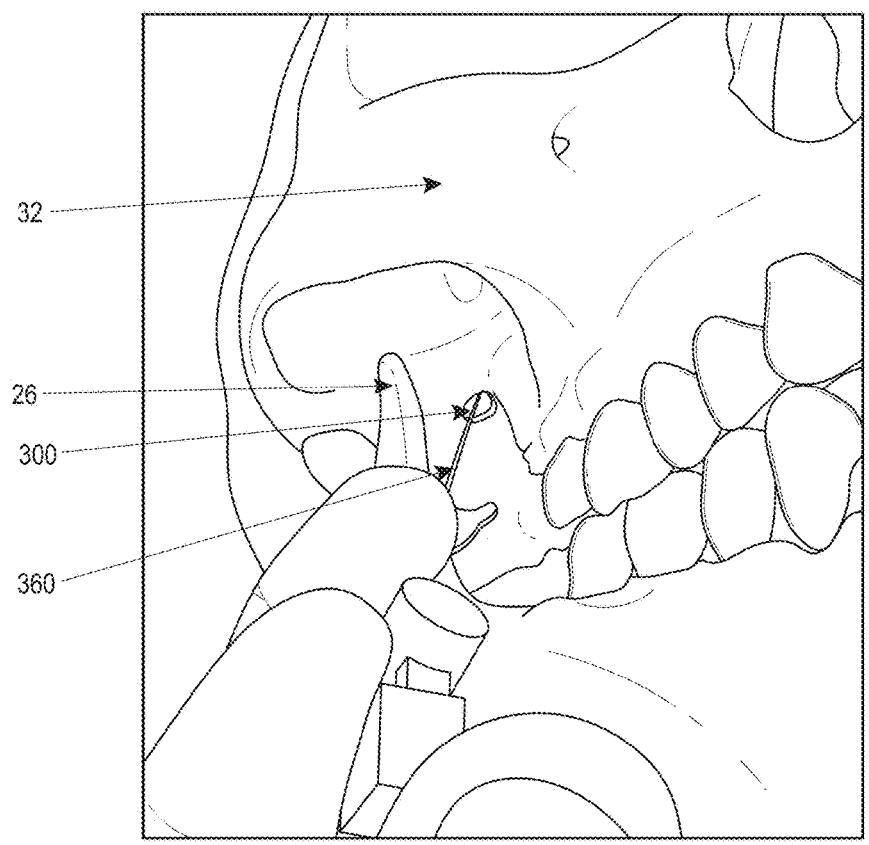

FIG. 7B illustrates a traditional approach to a trigeminal rhizotomy procedure, in which a needle 360 with an introducer (e.g., an electrode introducer) is inserted in close proximity to the oral cavity, and the foramen ovale 300 is cannulated. FIG. 7C illustrates the approach of FIG. 7B on a skeletal model, where cannulation of the foramen ovale 300 by a needle 360 can be seen, medial and inferior to the coronoid process 26. The zygomatic arch 32 is also illustrated.

Figure 7D:
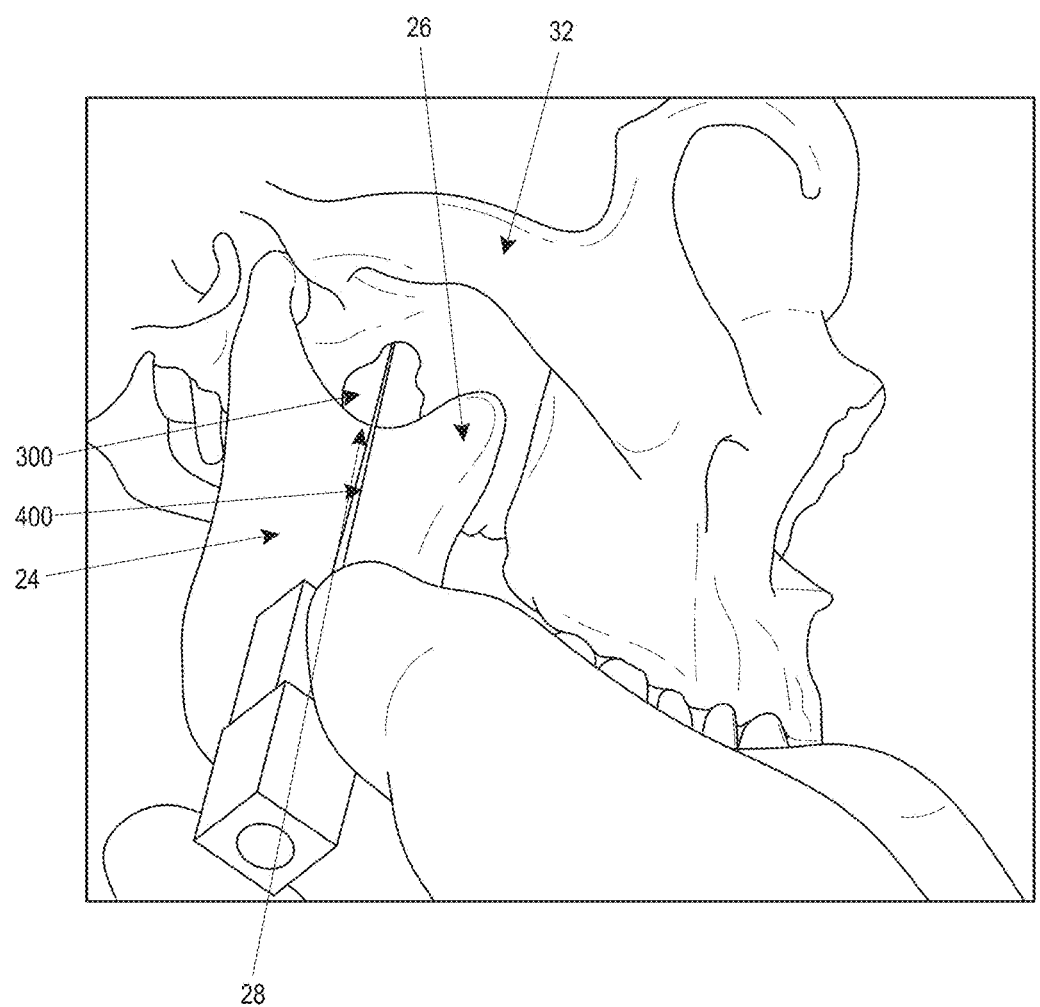
FIGS. 7D-7E illustrates a more lateral and/or superior approach to cannulating the foramen ovale proximate the coronoid process of the mandible, according to some embodiments of the invention.
Figure 7E:
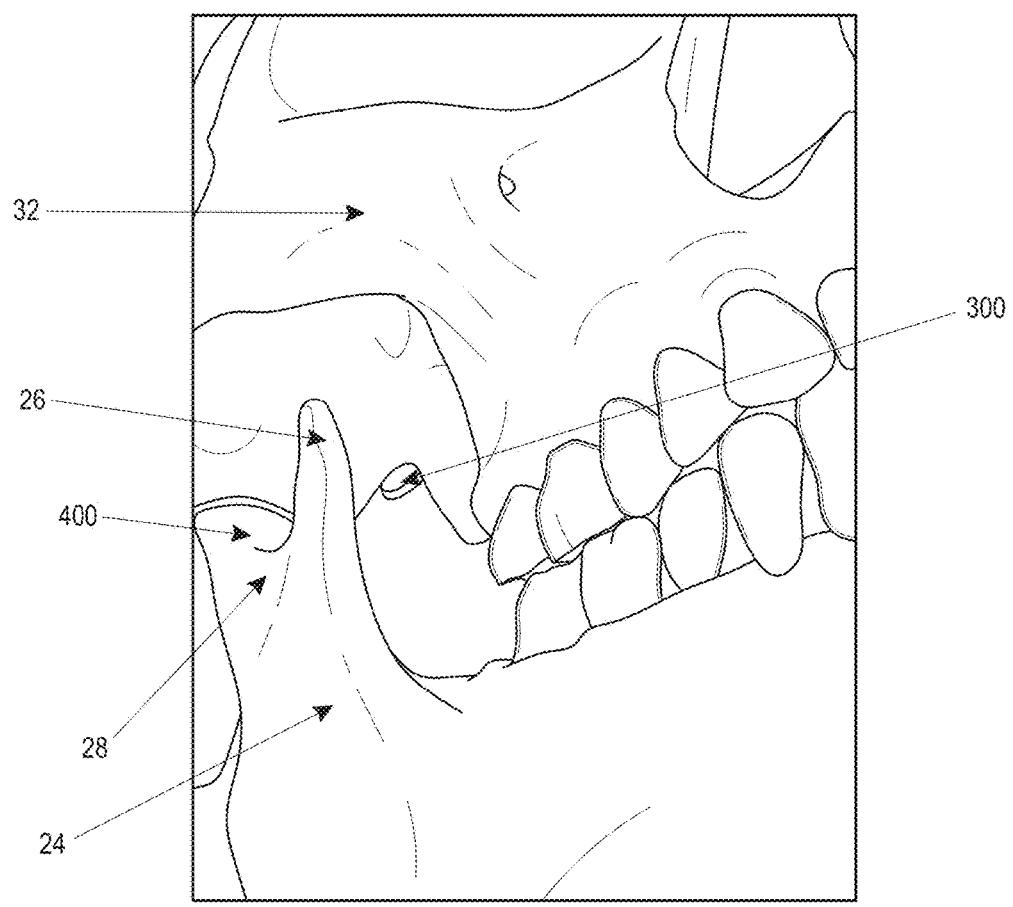
Figure 7F:
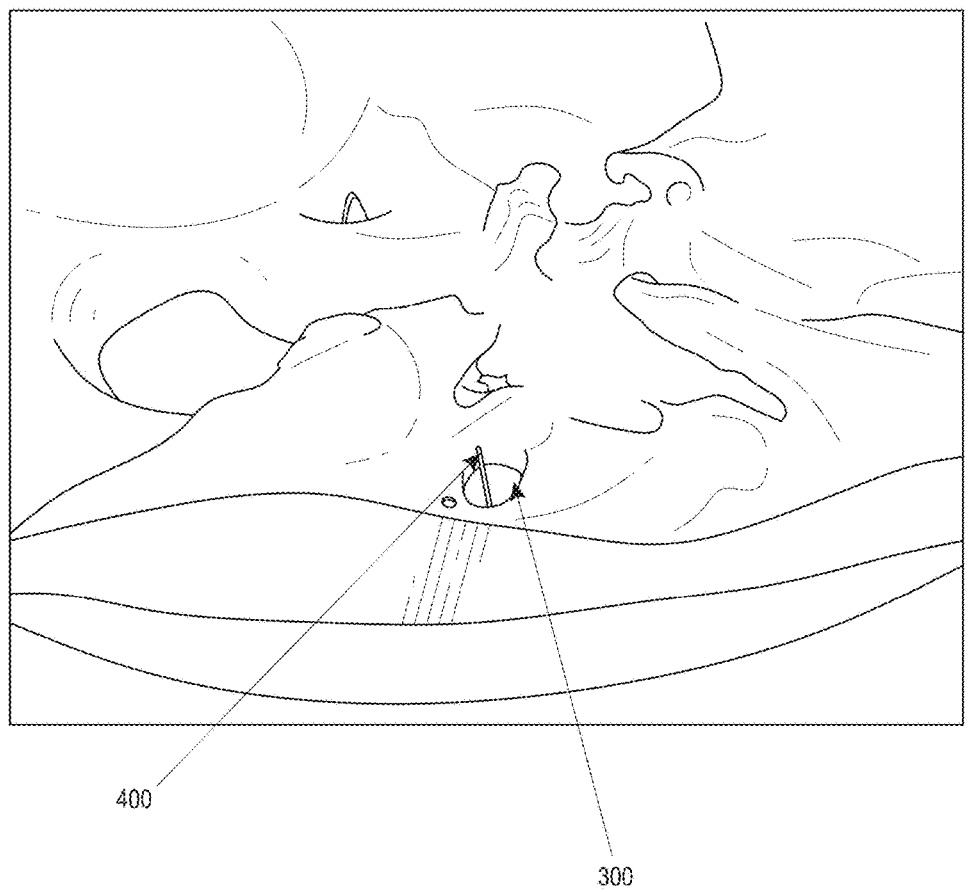
FIG. 7F is an intracranial view of the method of FIGS. 7D-7E, illustrating the tip of needle cannulating the foramen ovale and into the trigeminal ganglion (not shown).

FIG. 7D illustrates an advantageous, more lateral and/or superior approach to cannulating the foramen ovale 300 proximate the coronoid process 26 of the mandible 24, according to some embodiments of the invention. The patient is prepped and draped in a sterile fashion, and a needle 400 (such as part of a needle-catheter system for example) as described elsewhere herein can be inserted percutaneously proximate the coronoid process 26 of the mandible 24, and then advanced during an imaging modality such as fluoroscopy through the foramen ovale 300. In some embodiments, the needle tip can be percutaneously inserted within about 3 cm, 2.5 cm, 2 cm, 1.5 cm, 1 cm from (and in some cases lateral and/or superior to) the coronoid process 26 of the mandible 24 in a first direction (and superior to the mandibular notch 28, and inferior to the zygomatic arch 32). FIG. 7E is a more anterior angled view of FIG. 7D, illustrating the needle 400 cannulating the foramen ovale 300. The coronoid process 26 of the mandible 24 and the mandibular notch 28 are also illustrated. Upon cannulation of the foramen ovale 300 via the coronoid process 26 approach, a catheter 400, such as a conventional catheter or part of an all-in-one, integrated needle-catheter system described elsewhere herein can be advanced to perform a trigeminal rhizotomy procedure, such as a balloon rhizotomy, chemical rhizotomy, electromagnetic energy (e.g., RF or microwave) rhizotomy, and the like. FIG. 7F is an intracranial view of the method of FIGS. 7D-7E, illustrating the tip of needle 400 cannulating the foramen ovale 300 and into the trigeminal ganglion 302 (not shown).

Not to be limited by theory, there are several potential advantages of cannulation of the foramen ovale 300 percutaneously via the coronoid process 26 approach. For example, the distance from the skin to the foramen ovale 300 is about half the distance via the coronoid 26 approach (e.g., a distance of between about 2 cm and about 4 cm, or about 2.5 cm, 3 cm, or 3.5 cm), versus a traditional approach near the corner of the mouth. Avoiding the oral cavity completely, and being as far away as possible from the oral cavity can advantageously minimize introduction of oral flora/contaminants. Use of an integrated all-in-one needle catheter system as described herein can improve efficiency of procedure with time savings. Furthermore, when performing a balloon rhizotomy procedure, the balloon can have greater precision of deployment due to the presence of a catheter locking mechanism as described elsewhere herein.

Figure 8:
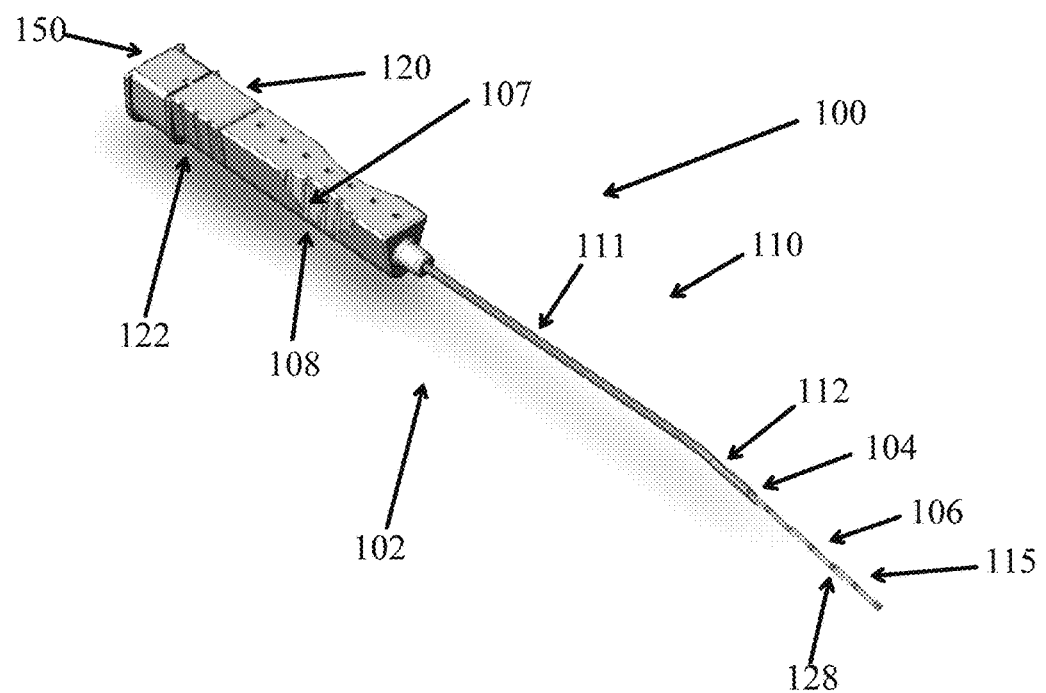
FIG. 8 is a schematic perspective view of a needle-catheter system according to some embodiments.

FIG. 8 illustrates a perspective view of a needle-catheter system 100 for accessing various anatomical locations, including the retro-orbital space, trigeminal ganglion, and the epidural space among others, according to some embodiments of the invention. The system 100 can include a needle 102, catheter 106, and stylet 150 (another embodiment of which is illustrated and described in connection with FIG. 8A below). The needle 102 can have a proximal hub 108, a proximal port (not shown) for connecting the needle 102 to the catheter 106, and a shaft portion 110 that includes a nondeflectable proximal shaft portion 111 and a distal shaft portion 112 that can be configured to be angled with respect to the proximal shaft portion 111, and deflectable in some embodiments. The needle 102 can have one or more lumens that can run from the proximal hub 108 through a length of the shaft 110 of the needle 102, to one or more distally or laterally-facing exit ports 104. In some embodiments, the deflectable distal portion 112 of the needle 102 can extend at a fixed angle with respect to the longitudinal axis of the nondeflectable portion 111 of the needle 102 (e.g., pre-bent). In other embodiments, the deflectable distal portion 112 of the needle 102 is actively steerable and adjustable through an angular range. The distal portion 112 can be angled to a maximum of, in some embodiments, between about 5° and about 20°, between about 10° and about 15°, or about 10°, about 15°, or about 20° in some embodiments relative to the longitudinal axis of the needle 102. In some actively steerable embodiments, one, two, or more pullwires can be operably connected, such as welded or otherwise attached to the deflectable distal portion 112 distally and a deflection control (not shown) proximally. A deflection control can be a knob, lever, or other control on the proximal hub 108 of the needle 102 or other area accessible by the physician. The needle 102 can have a sharp or atraumatic distal tip depending on the desired clinical result.

While embodiments above have described the needle 102 as having a steerable and/or curvable distal portion, in alternative embodiments, the entire shaft portion 110 of the needle is straight, while the catheter 106 is steerable or deflectable (e.g., made of a shape memory material and having a bent unconstrained state when not housed within a lumen of the needle 102, or steerable via an angular range through pullwires or another mechanism). In some embodiments, the shaft portion 110 of the needle is made of a biocompatible metal such as stainless steel. The shaft of the catheter 106 has in some embodiments an outer diameter less than that of the inner diameter of the needle shaft 110 to allow the catheter shaft to be housed completely within the needle shaft 110 during deployment of the catheter shaft to the retro-orbital space, trigeminal ganglion, epidural space, or other desired anatomical location. In some embodiments, the needle shaft 110 has an outer diameter or inner diameter of between about 15 Gauge and about 20 Gauge, such as about 15, 16, 17, 18, 19, or 20 Gauge in some embodiments.

In some embodiments, the outer diameter of the shaft of the needle 102 can be between about 1 mm and about 2 mm, such as between about 1.25 mm and about 1.75 mm, between about 1.40 mm and about 1.60 mm, or about 1.50 mm. In some embodiments, the inner diameter of the shaft of the needle 102 can be between about 0.90 mm and about 1.40 mm, such as between about 1.00 mm and about 1.30 mm, between about 1.10 mm and about 1.25 mm, or about 1.15 mm, 1.17 mm, or 1.20 mm.

In some embodiments, the outer diameter of the shaft of the catheter 106 can be between about 0.80 mm and about 1.10 mm, such as between about 0.90 mm and about 1.00 mm, or about 0.90 mm, 0.92 mm, 0.94 mm, 0.96 mm, 0.98 mm, or 1.00 mm.

In some embodiments, the inner diameter of the shaft of the catheter 106 can be between about 0.25 mm and about 0.75 mm, such as between about 0.40 mm and about 0.60 mm, between about 0.45 mm and about 0.55 mm, or about 0.50 mm, 0.52 mm, or 0.54 mm.

In some embodiments, the outer or inner diameter of the shaft of the stylet can be between about 0.20 mm and about 0.60 mm, between about 0.20 mm and about 0.40 mm, or between about 0.20 mm and about 0.30 mm, or about 0.20 mm, 0.22 mm, 0.24 mm, 0.26 mm, 0.28 mm, or 0.30 mm; or about 0.40 mm, 0.42 mm, 0.44 mm, 0.46 mm, 0.48 mm, or 0.50 mm.

Still referring to FIG. 8, the proximal hub 108 of the needle 102 can have an unlocked configuration allow for relative axial movement of the catheter 106 with respect to the needle 102. In some embodiments, the needle-catheter system 100 has a locked configuration which reversibly prevents relative axial movement between the catheter 106 and the needle 102 when the distal end of the catheter 106 extends distally past the distal end of the needle 102. This can be advantageous in some embodiments when the distal end 115 of the catheter 106 is positioned in, for example, the retro-orbital space, to ensure that the distal end 115 of the catheter 106 stays in position and does not migrate within the retro-orbital space or slip out of the retro-orbital space and back through the inferior orbital fissure during the diagnostic or therapeutic procedure. This can also be advantageous for other indications, such as to prevent the distal end 115 of the catheter 106 from migrating back proximally through the foramen ovale during a trigeminal rhizotomy procedure, or out of the epidural space for example. In some embodiments, the lock can include complementary male-female mating elements. In some embodiments, the lock can include threaded portions of the proximal hub 108 of the needle 102 and the proximal hub 120 of the catheter 106 include complementary threaded portions such that rotation of the proximal hub 108 of the needle 102 in an appropriate direction locks the needle 102 and the catheter 106 relative to each other.

In some embodiments, the proximal hub 108 of the needle 102 can be made of plastic or another polymer and include indented grooves 107 to enable manual gripping. The grooves 107 can be substantially transverse to the longitudinal axis of the needle 102 in some embodiments.

The proximal hub 108 of the needle 102 as well as the proximal hub 120 of the catheter 106 can have any appropriate cross-section, such as circular, triangular, square, or rectangular in some embodiments. In some embodiments, the cross-section is trapezoidal to facilitate gripping via a hemostat or other instrument. The catheter hub 120 can also include indented grooves 122 or other features as illustrated to facilitate manual gripping.

In some embodiments, the needle shaft 110 has an appropriate length such that the needle 102 can be percutaneously delivered to the sphenopalatine fossa, foramen ovale, epidural space, or other desired anatomical location. In some embodiments, the total length, or length of the nondeflectable portion of the needle shaft 110 has an axial length of between about 2 inches and about 4 inches, such as about 2 inches, 2.5 inches, 3 inches, 3.5 inches, or 4 inches. In some embodiments, the deflectable portion of the needle shaft 110 has an axial length of between about 0.5 cm and about 2 cm, or about 1 cm in some embodiments.

Still referring to FIG. 8, the distal end 115 of the catheter 106 extends distally from an exit port on the distal end 104 of the needle, such that it can extend an appropriate distance into the retro-orbital space and perform a desired diagnostic or therapeutic intervention. In some embodiments, the catheter 106 can extend distally between about 2 cm and about 5 cm relative to the distal end 104 of the needle 102, such as about 2 cm, 2.5 cm, 3 cm, 3.5 cm, 4 cm, 4.5 cm, 5 cm, or a range incorporating any of the aforementioned values. In some embodiments, the catheter 106 has an atraumatic distal tip and is configured to not be atraumatic to the contents of the orbit, a neural ganglion, or other tissue. The needle-catheter system 100 can have, in some embodiments, one or more radiopaque markers 128 for visualization under fluoroscopy. In some embodiments, the distal end 115 of the catheter 106 can include a plurality of radiopaque markers spaced evenly apart by a preset distance, such as every 0.5 cm or every 1 cm for example, to provide the physician with indicia of the location of the catheter 106 within the retro-orbital space, trigeminal ganglion, epidural cavity, or other desired anatomical location. In some embodiments, the distal end 115 of the catheter 106 can be operably connected to a source of a therapeutic agent, such as a medicament as described elsewhere herein.

Figure 8A:
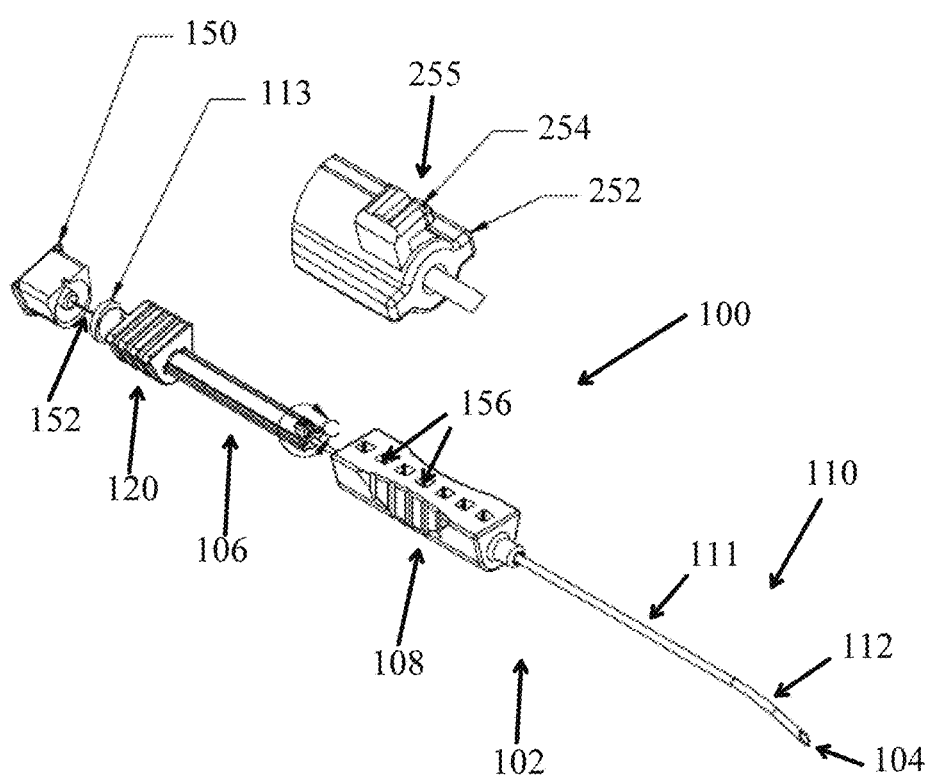
FIG. 8A is a schematic perspective view of another needle-catheter system according to some embodiments.

FIG. 8A illustrates a schematic exploded view of an embodiment of a needle-catheter system 100 that includes some features that are similar to that shown in FIG. 8. Illustrated is needle 102 including proximal hub 108 and shaft 110. The catheter 106 can be inserted into a proximal port on the proximal hub 108 of the needle that can be coaxial with the longitudinal axis of the needle. The catheter 106 is shown with a proximal hub 120 with a trapezoidal cross-section for ease of rotation with a hemostat as previously described. The proximal hub 120 of the catheter 106 can include an input port on its proximal end such as a luer lock 113 as shown. A stylet 150 can have a stylet shaft 152 that can be a solid tubular member in some embodiments that runs axially along the entire length or substantially along the entire length of the lumen of the catheter shaft. The stylet can have a threaded surface on its distal end such that it can be reversibly attached to the input port 113 on the proximal hub 120 of the catheter 106. The stylet shaft 152 can advantageously prevent backflow of bodily fluids, tissue or other debris that could clog the catheter lumen prior to deployment within the retro-orbital space. Once the distal end of the catheter 106 is deployed within the retro-orbital space, the stylet can be withdrawn, allowing the lumen of the catheter shaft 106 to be ready for use. As described in connection with FIG. 8, the proximal hub 108 of the needle 102 can be configured to reversibly lock with the catheter hub 120. In some embodiments, the lock can include threaded portions of the proximal hub 108 of the needle 102 and the proximal hub 120 of the catheter 106 include complementary threaded portions such that rotation of the proximal hub 108 of the needle 102 in an appropriate direction locks the needle 102 and the catheter 106 relative to each other. In some embodiments, as illustrated in the detail view of the distal end of the catheter hub 120, the needle-catheter lock includes a snap lock 255. The snap lock 255 can include a biased movable surface 254 configured to move up and down in a direction transverse to the longitudinal axis of the catheter 106 and the needle 102. When the catheter 106 is moved distally into a channel of the proximal hub 108 of the needle 102, the moveable surface 254 of the snap lock 255 can snap through one, two or more apertures 156 spaced axially regularly or irregularly apart along the proximal hub 108 of the needle 102, locking the catheter 106 with respect to the needle 102. In some embodiments, the apertures 156 can be spaced apart by between about 0.25 mm and about 1 mm, such as about 0.5 mm in some embodiments. Applying a force on the moveable surface 254 of the snap lock 255 while it protrudes out of one of the apertures 156 can allow for axial movement of the catheter 106 with respect to the needle 102. In this manner, the snap lock 255 allows the catheter 106 to move axially either distally or proximally in a stepwise fashion between adjacent apertures 156. In some embodiments, a single aperture 156 is present on the proximal hub 108 of the needle 102 allowing for a single locking position. The snap lock 255 can also include one, or a plurality of anti-overrotation tabs 252 that prevents excess rotation of the catheter 106 within a channel of the proximal hub 108 of the needle 102. The channel can be configured to allow limited rotation in some embodiments, but when the anti-overrotation tab 252 meets a stop surface within the channel, excess rotation can be prevented. In some embodiments, the channel can allow for no more than about 90, 85, 80, 75, 70, 65, 60, 55, 50, 45, 40, 35, 30, 25, 20, 15, or 10 degrees of rotation for example. In addition to threaded and snap-lock locking features as described, complementary magnets, clamps, and other reversible locking mechanisms can also be utilized to reversibly lock the proximal hub 108 of the needle to the proximal hub 120 of the catheter 106. Such all-in-one needle catheter systems as described herein can advantageously simplify procedures and reduce procedure time, as the needle, catheter, and hub are pre-connected in a seamless manner. The controllability of catheter deployment is also enhanced by the ability of the catheter 106 and needle 102 to lock together into place.

Figure 8B:
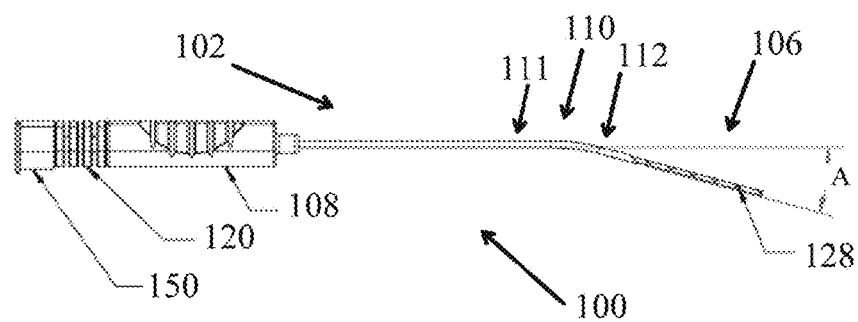
FIGS. 8B-8F illustrate various views of the needle-catheter system of FIG. 8A.

FIG. 8B illustrates a side view of the needle-catheter system 100 illustrated in FIG. 8A. In some embodiments, the catheter can be radiopaque and configured to extend up to about 2 cm, 2.5 cm, 3 cm, 3.5 cm, or 4 cm beyond tip of the needle, with indicia of length, such as markings, such as at evenly spaced-apart 0.5 cm or 1 cm intervals for example, as illustrated.

Figure 8C:
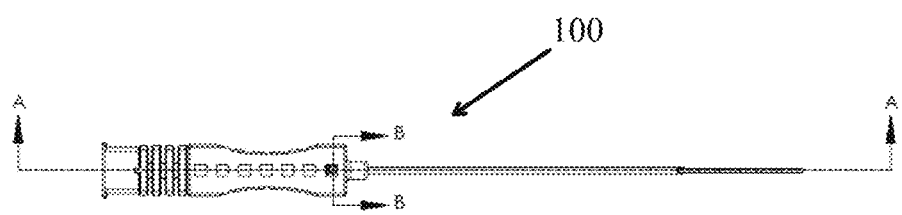
Figure 8D:
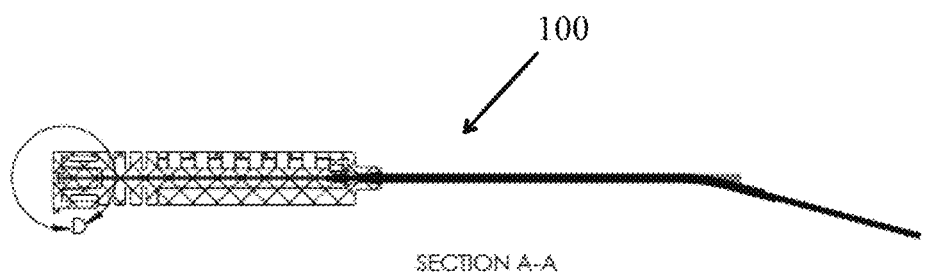
Figure 8E:
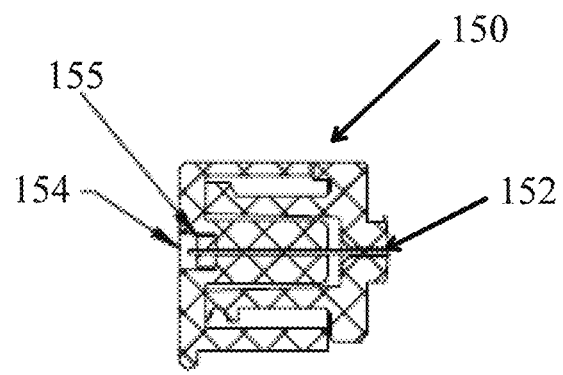
Figure 8F:
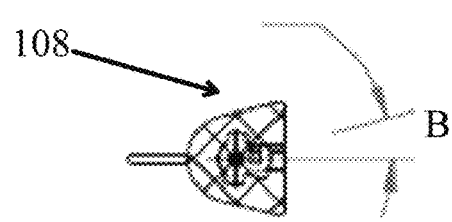

FIG. 8C illustrates a schematic view of the needle-catheter system 100 of FIGS. 8A-8C. FIG. 8D illustrates a longitudinal cross-sectional view of the needle catheter system 100 through line A-A of FIG. 8C. FIG. 8E is a close-up detail view of area D of FIG. 8D, illustrating a cross-sectional view of the proximal end 154 of the stylet 150. As shown, the stylet 150 can include a crimp 155 to fix the proximal end of the shaft 152 to the stylet 150, and further attached via an adhesive in some embodiments near 154. FIG. 8F is a transverse cross-sectional view through line B-B of FIG. 8C. As previously described, rotating the proximal hub 108 of the needle 102 or the proximal hub 120 of the catheter 106 in an appropriate direction or counter-direction (e.g., in direction of arrows near B) prevents or allows for relative movement of the catheter 106 with respect to the needle 102.

The needle-catheter system can include a first configuration where the shaft of the catheter is housed completely within the shaft of the needle, such as prior to use or when the needle-catheter system is being deployed to the sphenopalatine fossa or other desired anatomical location. The needle-catheter system can also include a second configuration where the distal end of the catheter extends distally beyond the exit port of the needle and the proximal hub of the needle is locked to the proximal hub of the catheter, preventing axial movement of the catheter with respect to the needle.

Figure 8G:
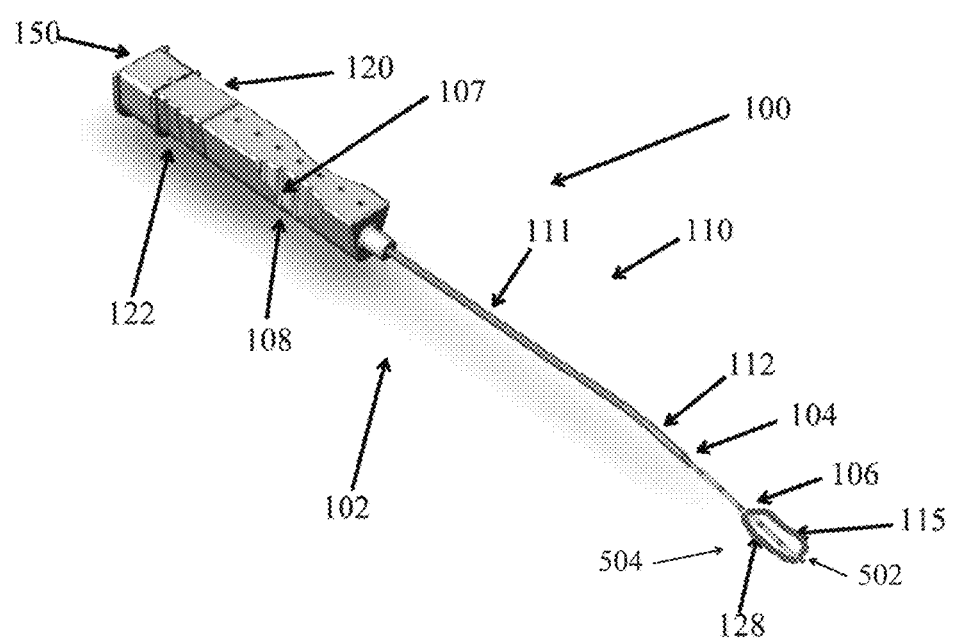
FIG. 8G schematically illustrates a needle-catheter system that can be as previously described in connection with FIGS. 8-8F for example, but also includes one, two, or more expandable elements.

FIG. 8G schematically illustrates a needle-catheter system 500 that can be as previously described in connection with FIGS. 8-8F for example, but also includes one, two, or more expandable elements. The expandable element can be, for example, an inflatable balloon 502. The balloon 502 can be secured at a distal neck 504 to the distal end of the catheter as is understood in the balloon catheter arts. The distal neck 504 may extend distally from the balloon, as illustrated, or may invert and extend proximally along the tubular body. In either event, the distal neck 504 of the balloon 502 can be provided with an annular seal either directly to the catheter or to a polymeric liner positioned concentrically about the tubular body, depending upon the particular device design. This will provide an isolated chamber within balloon 502, which is in fluid communication with a proximal source of inflation media by way of an inflation lumen. The balloon 502 can have any desired configuration, and can be pear-shaped in some embodiments. A pear-shaped balloon may, in some cases, improve outcome and correspond to the inner anatomy of the Meckel cave—the distal protrusion surrounding the trigeminal ganglion 302 and the distal part of the trigeminal root 304 as previously described. However, axially symmetric balloons can also be utilized. A pear-shaped balloon can have a distal zone with a first relatively narrower diameter, and a proximal zone with a second relatively wider narrower and a bulbous shape. In some embodiments, the balloon 502 is provided with an elongate tubular proximal neck which extends throughout the length of the needle-catheter system 500, to a proximal port or other site (not shown) for connection to a source of inflation media. This part can be blow molded within a capture tube as is well understood in the balloon catheter arts, to produce a one piece configuration. Alternatively, the balloon can be separately formed and bonded to a tubular sleeve. During assembly, the proximal neck or outer sleeve may conveniently be proximally slipped over the catheter, and secured thereto, as will be appreciated by those of skill in the catheter manufacturing arts. In some embodiments, the balloon 502 has a lubricous coating that can be chemically bonded or physically coated.

In some embodiments, yet another indication for an integrated, all-in-one needle-catheter system as described elsewhere herein is accessing the epidural space (or intrathecal access via a spinal catheter in other embodiments), for injection of a contrast agent, anesthetic agent (e.g., lidocaine, mepivacaine, bupivacaine, ropivacaine, or chloroprocaine), anti-inflammatory agent (such as a glucocorticoid or non-steroidal anti-inflammatory agent), opioid, or other diagnostic or therapeutic agent such as an agent described elsewhere herein for example.

Needle-catheter systems as described herein can also be utilized for withdrawal of tissue or fluid, such as for biopsy purposes or drainage of an abscess or hematoma for example. In some embodiments, systems and methods can be used to deliver an end effector through or operably connected to the catheter to deliver, for example, electrical stimulation, electromagnetic stimulation, RF, microwave, thermal, cryo, ultrasound, or other energy sources to the epidural space, or other target locations as described herein. The catheter can also be used as a conduit to deliver a diagnostic and/or therapeutic medical device permanently or temporarily to the target location.

In some embodiments, the needle-catheter systems and access methods as described herein can be utilized for the controlled stimulation or ablation of spinal and paraspinal nerve root ganglia, or sympathetic or parasympathetic nerves to treat pain, spasticity, post-herpetic neuralgia, phantom lib pain, neuropathic pain, or a variety of other indications and conditions. In some embodiments, the ganglion is a dorsal root ganglion (DRG). In some embodiments, one, two, or more electrodes could be advanced substantially adjacent to a peripheral nerve toward a ganglion such as a DRG, and the electrodes activated to stimulate a portion of the DRG. The electrodes could be provided, for example, via an elongate member delivered through a lumen of the catheter, or be operably attached to the outside diameter of the catheter itself in some embodiments. Stimulation systems and methods as disclosed for example in U.S. Pat. No. 7,580,753 to Kim et al., and U.S. Pub. No. 2011/0276056 to Grigsby et al., both of which are incorporated by reference in their entireties can be utilized or modified for use with needle-catheter systems as disclosed herein. In some embodiments, electrode placement accuracy can be enhanced by first placing a catheter near the targeted spinal nerve root or other location, and then visualized the nerve root or other location with contrast medium, and then placing the electrode wire through the lumen of the catheter onto the visualized nerve root, similar to a Seldinger technique.

Figure 9:
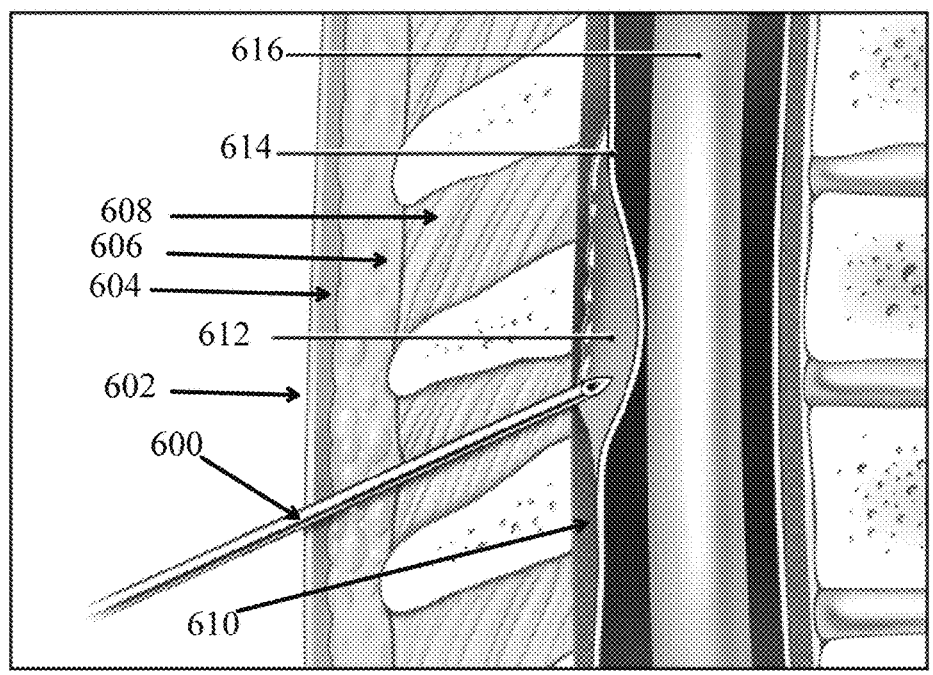
FIG. 9 illustrates percutaneous access of a needle (or needle-catheter system) into the epidural space.

FIG. 9 schematically illustrates percutaneous access of a needle-catheter system 600 through the skin 602, subcutaneous fascia 604, supraspinous ligament 606, interspinous ligament 608, and ligamentum flavum 610, and then into the epidural space 612. Illustrated deep to the epidural space 612 is the dura mater 614 and the spinal cord 616. Conventional epidural catheter systems, such as those by Epimed International (Farmers Branch, Tex.), have separate components which need to be assembled to perform the procedure, such as a discrete needle, catheter, and hub, all components that can be detached from one another. As noted above, integrated, all-in-one needle catheter systems as described herein can advantageously simplify epidural and spinal procedures and reduce procedure time, as the needle, catheter, and hub are pre-connected in a seamless manner. The controllability of catheter deployment is also enhanced by the ability of the catheter and needle to lock together into place.

Figure 10:
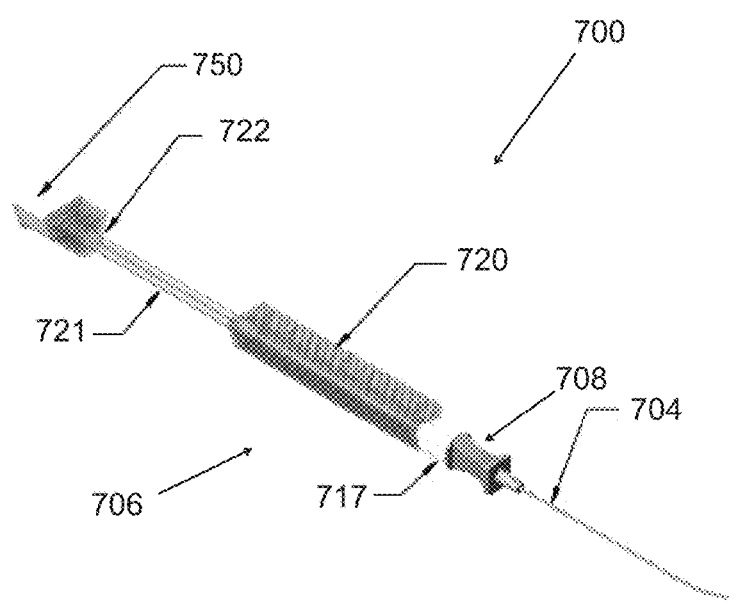
FIGS. 10-11F illustrate views of a needle-catheter system including a rotatable lock boss feature, according to some embodiments of the invention.

FIG. 10 illustrates a perspective view of another needle-catheter system 700 for accessing various anatomical locations, according to some embodiments of the invention. The system 700 can include a needle 704, catheter 706, and stylet 750. The needle 704 can include a proximal hub 708 with a lumen configured to house a portion of a catheter shaft (not shown) therethrough. The needle 704 could have a straight or a curved distal end in some embodiments. The catheter 706 could include a proximal hub 722 with a lumen configured to fit a stylet wire therethrough. The proximal hub 722 of the catheter 706 is connected, e.g., integrally attached to an elongate catheter holder 721 distal to the catheter hub, which is operably connected distally to the catheter shaft (not shown). The catheter hub 722, catheter holder 721, and catheter shaft can be configured to move axially with respect to a catheter handle 720 with complementary locking features. Rotation/twisting of the catheter hub 722 with respect to the catheter handle 720 in an appropriate direction can reversibly axially lock and unlock the catheter hub 722 (and the distal catheter shaft). Also illustrated between the catheter handle 720 proximally and the needle hub 708 distally is a male luer with a spinning luer lock ring 717 configured to lock and unlock the catheter handle 720 from the needle hub 708.

Figure 11A:
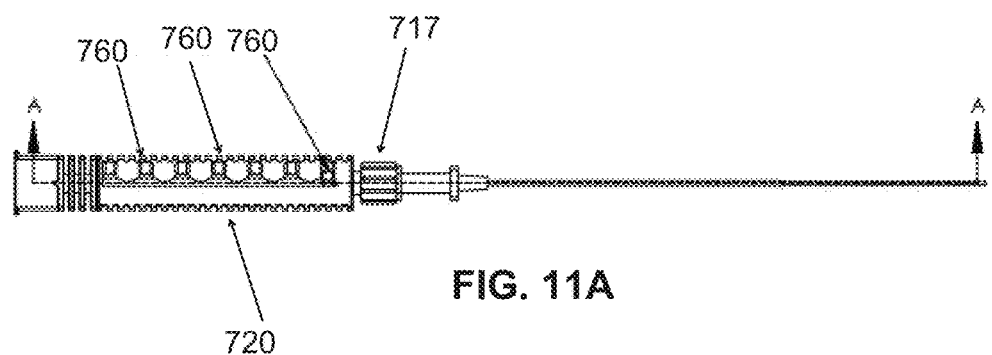
FIGS. 11G-11L illustrate views of a needle-catheter system including an axially movable friction lock control, according to some embodiments of the invention.
FIGS. 11M-11S illustrate views of a needle-catheter system including a collet lock, according to some embodiments of the invention.
Figure 11B:
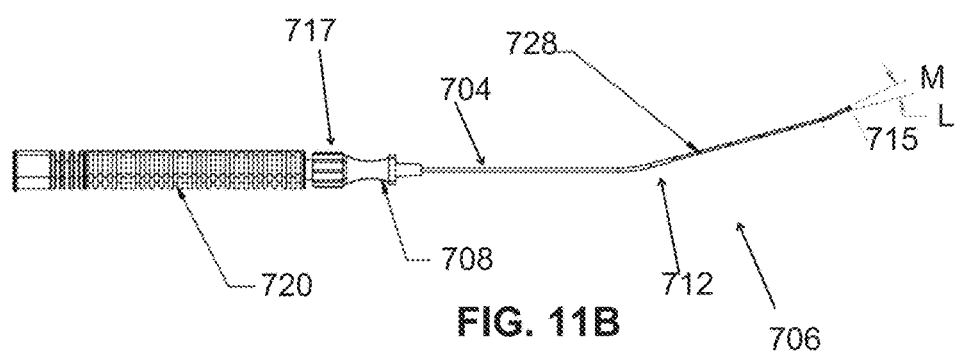
Figure 11C:
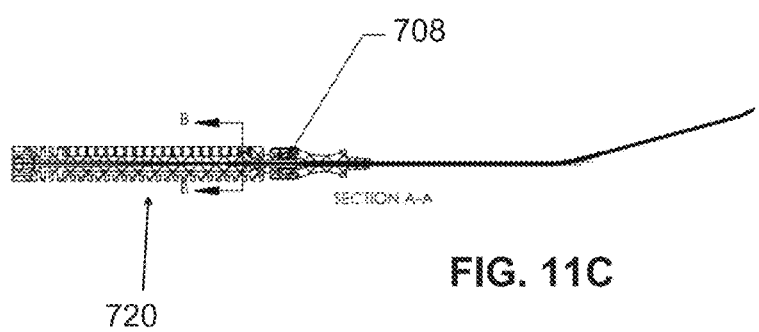
Figure 11D:
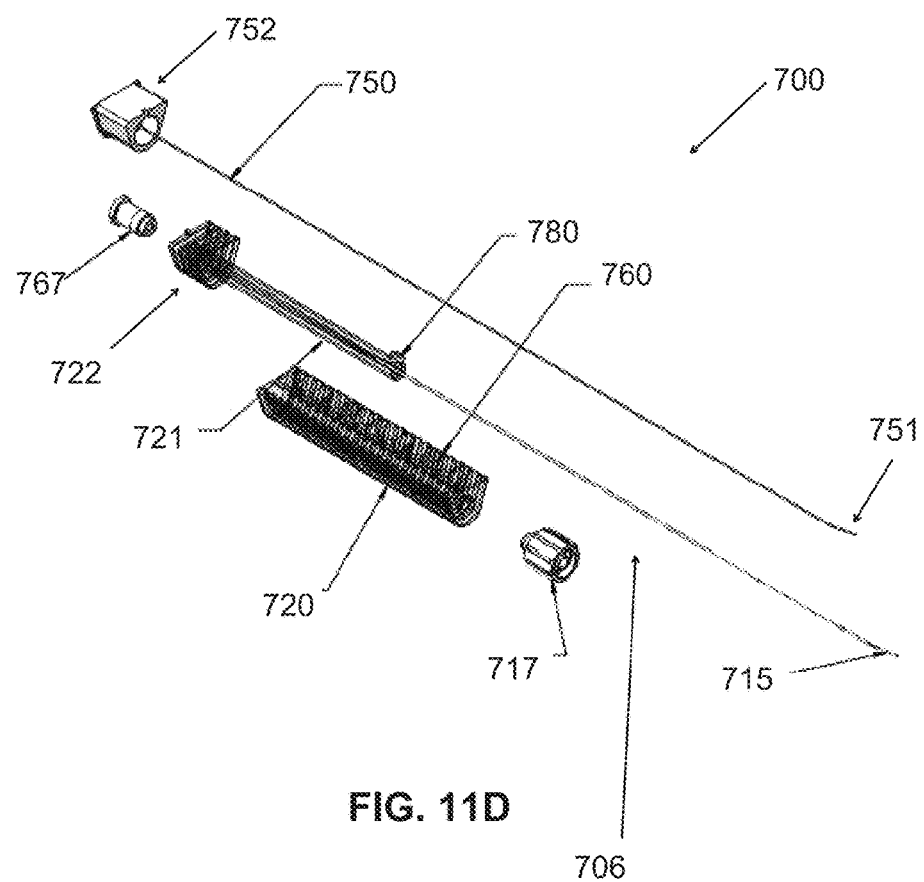
Figure 11E:
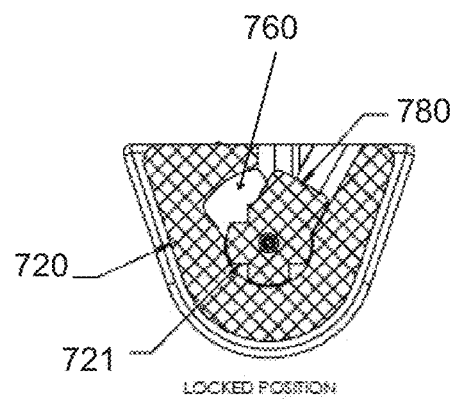

FIG. 11A is a cross-sectional side view of the needle-catheter system of FIG. 11, illustrating that the catheter handle 720 has axially-spaced apart catheter lock position features 760, such as slots or grooves for example. The lock position features 760 could be, for example, spaced regularly 1 cm apart from each other, or at other intervals or irregularly spaced apart in some embodiments. FIG. 11B illustrates another view of the needle-catheter system 700, illustrating needle 704 with a curved distal end 712, and catheter 706 extending distally from the distal end 712 of the needle 704. The distal end 715 of the catheter 706, such as the distal 0.5 cm to 2 cm, or distal 1 cm in length in some embodiments can be bent or otherwise curved at an angle M to that of the longitudinal axis L of a more proximal segment of the catheter 706. The angle M could be, e.g., between about 5 degrees and about 25 degrees, such as about 5, 10, 15, 20, or 25 degrees in some embodiments. Also illustrated are radiopaque markers 728 which can be spaced apart, such as at 1 cm intervals. In some embodiments, the catheter can extend approximately 5-7 cm in length distally past the distal end 712 of the needle, such as about 6 cm, of which the curved or bent distal end of the catheter is about 1 cm in length. FIG. 11C is a cross-section through lines A-A of FIG. 11A. In some embodiments, a male luer tip 708 can be configured to allow for handle rotation when the luer lock is relatively tight. In some embodiments, the needle has an outside diameter of between about 1.0 mm and about 1.5 mm, such as about 1.27 mm; and the catheter has an outer diameter of between about 0.6 mm and about 1.0 mm, such as about 0.84 mm. FIG. 11D is an exploded view of various components of the needle-catheter system of FIGS. 11A-11C. Illustrated is stylet 750 including proximal stylet hub 752 and distal stylet wire. In some embodiments, a distal segment 751 of the stylet 750 has a curved or bent tip to facilitate steering of the catheter. The curved or bent tip could be angled, for example, between 5 degrees and about 20 degrees, such as about 10 degrees with respect to a more proximal portion of the stylet wire. Also illustrated is a female luer 767 connected proximally to catheter hub 722, elongate catheter holder 721 coupled to catheter shaft 706 with angled tip 715 as previously described. The distal end of the catheter holder 721 can include a radially extending lock boss 780 to facilitate reversible locking and unlocking of the catheter hub 722, catheter holder 721, and catheter 706 to the catheter handle 720. Catheter handle 720 can include lock position features 760 as previously described. A male luer lock 717 can connect the catheter handle 720 with the needle (not shown) as previously described. FIG. 11E illustrates a cross-sectional view illustrating catheter handle 720 with a axially extending lumen configured to house the distal end of the catheter holder 721 with radially extending lock boss 780 reversibly locked within a groove or slot of the lock position feature 760. As shown, the flat outer surfaces of the catheter handle 720 can be aligned with that of the catheter holder 721. FIG. 11F illustrates a cross-sectional view illustrating catheter holder 721 with lock boss 780 in an unlocked position, and rotated with respect to the catheter handle 720. The degree of rotation to lock and unlock can be any desired angle FF, such as between about 15 degrees and about 90 degrees in some embodiments, such as between about 30 degrees and about 80 degrees, or about 55 degrees.

Figure 11F:
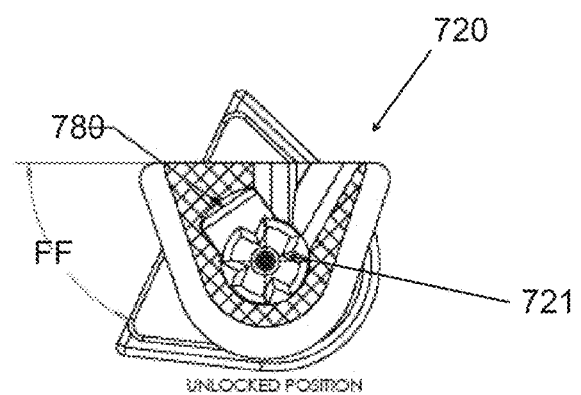
Figure 11G:
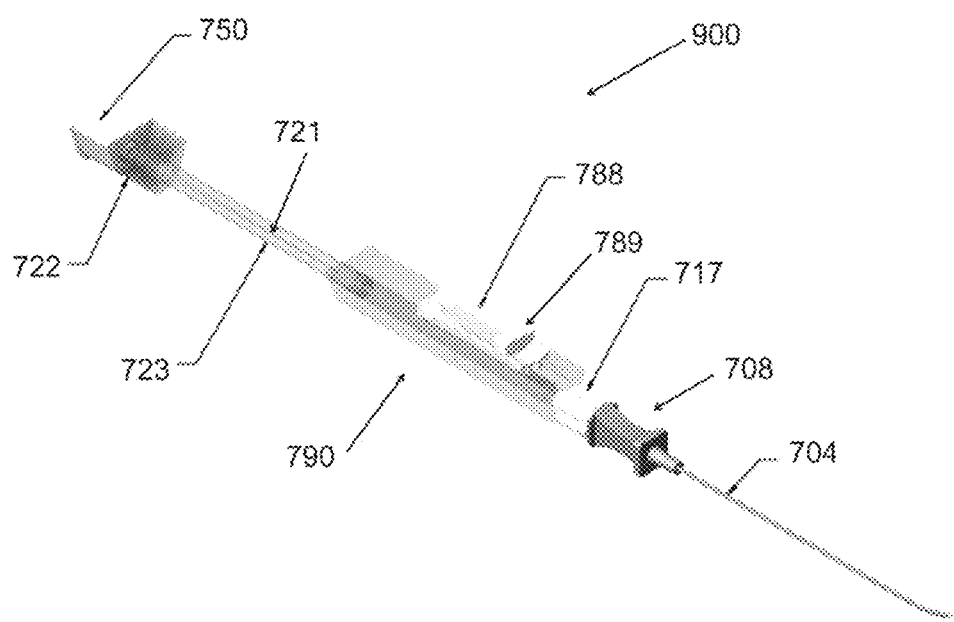
Figure 11H:
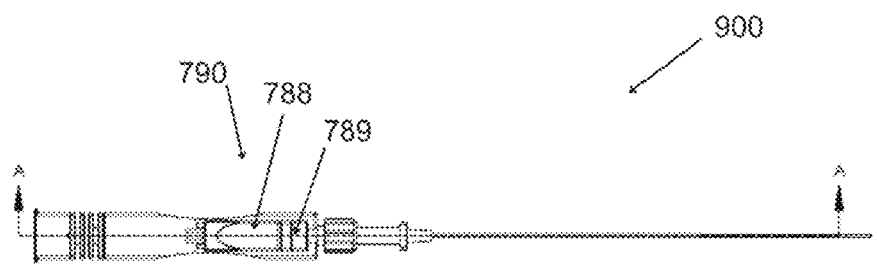
Figure 11I:
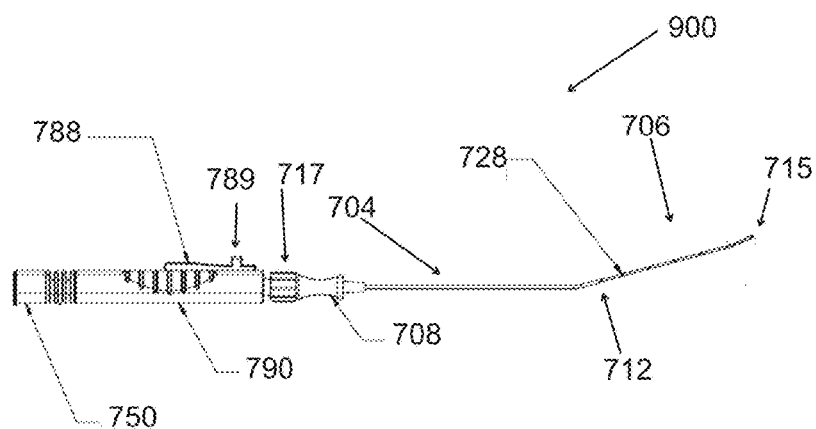
Figure 11J:
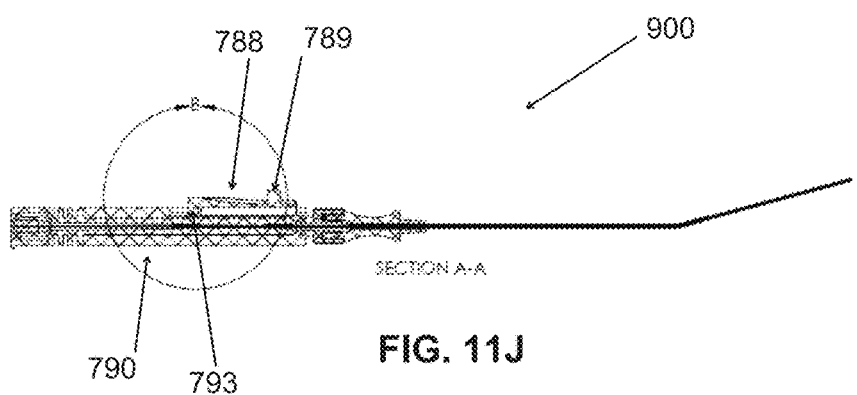
Figure 11K:
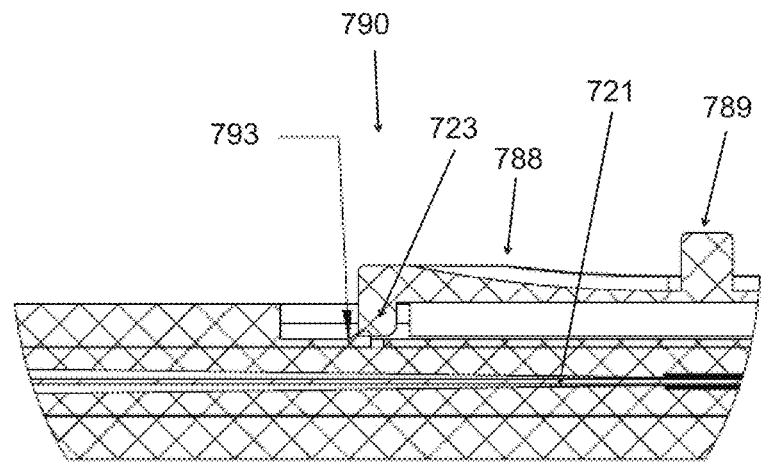
Figure 11L:
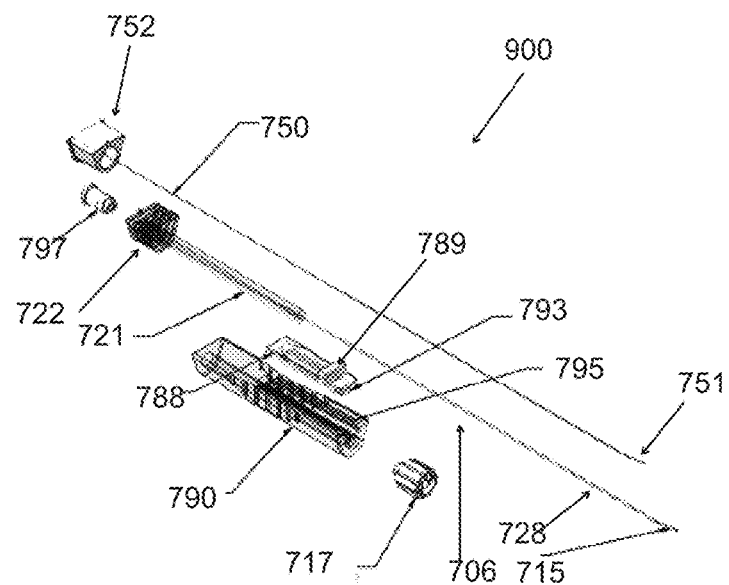

FIG. 11G illustrates another embodiment of a needle-catheter system 900, which can include some features similar to or as previously described in connection with FIGS. 10-11F above. Elongate catheter holder 721 can include a protective outer sheath 723 with a friction lock surface configured to provide a friction fit with a complementary surface of a locking surface of the catheter handle 790. The catheter handle 790 can include a friction locking mechanism 788 including a movable control 789. The control 789 can be, for example, a radially outwardly extending, axially slidable tab as illustrated, that is operably attached to a flexible, radially inwardly extending friction nub 793 as illustrated and described further below. The catheter handle 790 can attach securely to the needle hub 708 of the needle 704 via, for example, a male luer with a spinning luer lock ring 717. However, the catheter shaft can still in some configurations move axially with respect to the needle hub 708 and needle 704 as the axial locking mechanism for the catheter shaft with respect to the needle can be different from and spaced apart from the luer lock ring 717 (e.g., friction locking mechanisms, collet locks, etc. as described elsewhere herein). In some embodiments, the luer lock ring 717 is configured not to rotate when the luer lock is tight. Movement of the control 789 axially, e.g., in a distal direction can increase friction from the radially inwardly extending friction nub 793 with respect to the sheath 723 of the catheter holder 721, locking the catheter at a desired position, such as, for example, at any position indicating that the distal end of the catheter extends between about 3 cm and about 6 mm distally from the distal end of the needle in some embodiments. In other words, the catheter can be axially locked with respect to the needle as well. FIG. 11H illustrates a top view of the needle-catheter system 900 of FIG. 11G, and in particular the catheter handle 790, friction locking mechanism 788, and control 789. FIG. 11I illustrates a side view of FIG. 11H, including catheter friction locking mechanism 788 and slidable locking control 789. The catheter can also include spaced-apart radiopaque markers and an angled curved or bent tip as previously described. FIG. 11J illustrates a cross-section through line A-A of FIG. 11H, including friction locking mechanism 788 and movable control 789 on the catheter handle 790, as well as flexible friction nub 793 which can create a friction lock with outer sheath 723 of the catheter holder 721. FIG. 11K is a close-up view of area B of FIG. 11J. FIG. 11L is an exploded perspective view of various components of the needle-catheter system 900, including proximal stylet hub 752 of stylet 750, and distal stylet wire. A distal end 751 of the stylet 750 can be angled (e.g., curved or bent) with respect to a more proximal segment of the stylet 750 to assist in steering the catheter 706 as previously described. The stylet 750 can be withdrawn when the catheter 706 is in a desired position, so items can be delivered (e.g., infused or moved distally through) the catheter 706 or withdrawn (e.g., aspirated or moved proximally out of the catheter) through female luer 797 on the proximal end of the proximal catheter hub 722. The catheter handle 790 with locking mechanism 788, control 789 connected to friction nub 793, and a axially extending groove with proximal and distal stops to limit the axial travel of the control 789 are also illustrated.

Figure 11M:
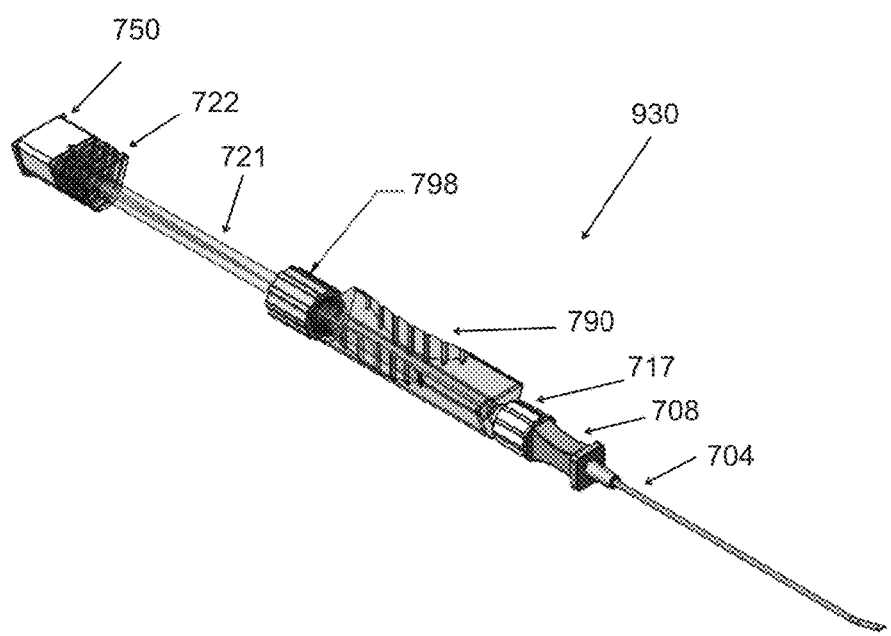
Figure 11N:
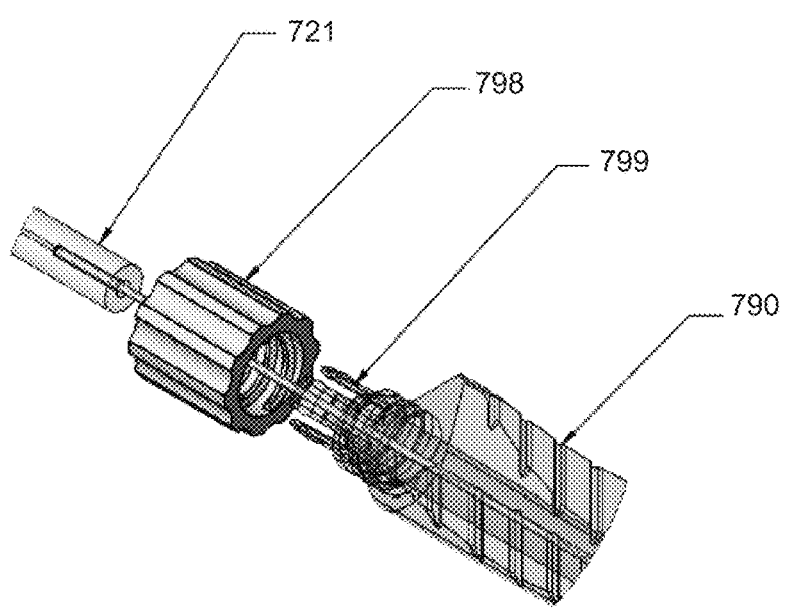
Figure 11O:
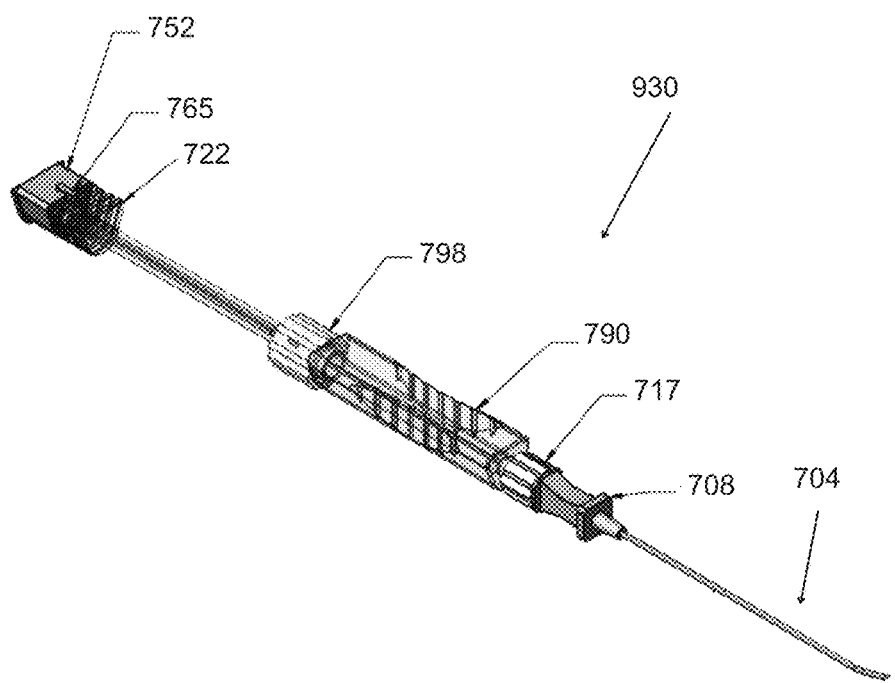
Figure 11P:
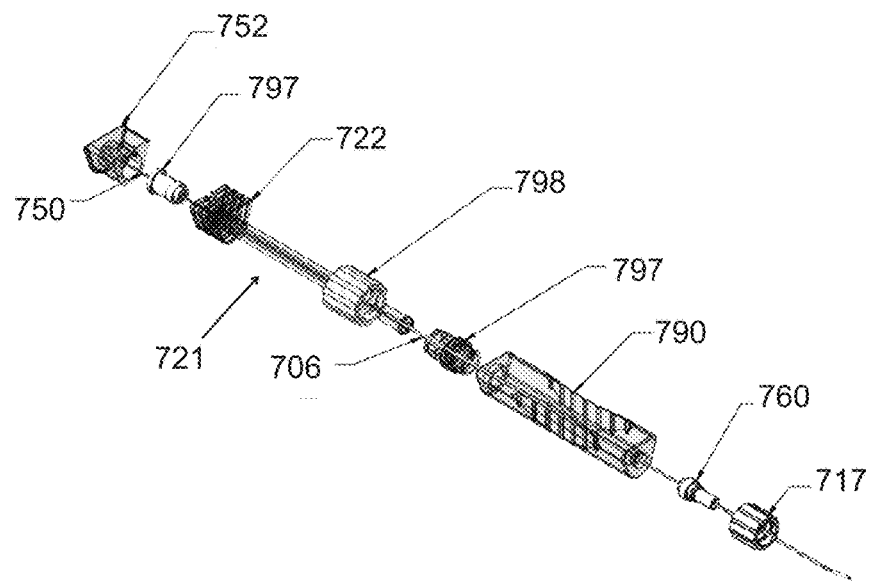
Figure 11Q:
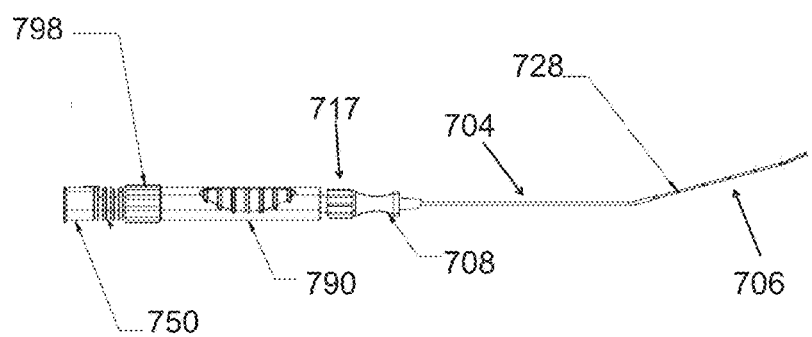

FIG. 11M illustrates another embodiment of a needle catheter system 930, which can include some features similar to or as previously described in connection with FIGS. 11G-11L above. Rather than a friction lock, the locking mechanism can be a collet, including a collet nut 798 with axial grooves on its outer surface and a threaded inner surface, and configured when rotated in an appropriate direction to engage with a collet lock 799 operably connected distally to catheter handle 790. Doing so can lock the catheter holder 721 and associated catheter 706 in a reversibly locked axial position with respect to the catheter handle 790 as well as the needle 704, via static friction from the interaction of the collet nut 798 and collet lock 799. The collet lock 799 can be positioned and the collet nut 798 are positioned adjacent to and proximal to the catheter handle 790 as shown. FIG. 11N illustrates a close-up view of the catheter holder 721, collet nut 798, collet lock 799, and catheter handle 790. FIGS. 11O-11Q illustrate additional views of a needle-catheter system 930 with a collet lock. Proximal stylet hub 752 as shown can include an orientation tab 765 or other indicia or orientation with respect to the catheter. As previously described, turning the collet nut 798 in an appropriate direction locks the catheter and associated catheter in place, such that the catheter is reversibly axially locked in place with respect to the needle. The catheter can also include spaced-apart radiopaque markers and an angled curved or bent tip as previously described. As shown, the collet nut and lock allows the catheter to be advantageously in some embodiments axially locked to the needle proximal to the catheter handle 790 of which the catheter shaft travels therethrough, and spaced apart proximally from the proximal hub 708 of the needle 704; the collet nut and lock may not be directly attached to the needle.

In some embodiments, a needle-catheter system can include an 18 Gauge needle configured to fit a 21 gauge catheter therethrough. In some embodiments, the needle can have an outer diameter of between about 1 mm and about 1.5 mm, such as between about 1.2 mm and about 1.3 mm, such as about 1.27 mm; the needle can have an inner diameter of between about 0.8 mm and about 1.3 mm, such as between about 0.95 mm and about 1.15 mm, or about 1.07 mm; the catheter can have an outer diameter of between about 0.6 mm and about 1 mm, such as about 0.84 mm; the catheter can have an inner diameter of between about 0.4 mm and about 0.8 mm, such as about 0.58 mm; and the stylet can have an outer diameter of between about 0.3 mm and about 0.5 mm, such as about 0.43 mm.

In some embodiments, a needle-catheter system can include a 16 Gauge needle configured to fit a 19 Gauge catheter therethrough. In some embodiments, the needle can have an outer diameter of between about 1.4 mm and about 1.9 mm, such as between about 1.6 mm and about 1.7 mm, such as about 1.65 mm; the needle can have an inner diameter of between about 1 mm and about 1.5 mm, such as between about 1.3 mm and about 1.4 mm, or about 1.35 mm; the catheter can have an outer diameter of between about 1 mm and about 1.4 mm, such as about 1.22 mm; the catheter can have an inner diameter of between about 0.8 mm and about 1.1 mm, such as about 0.97 mm; and the stylet can have an outer diameter of between about 0.7 mm and about 0.9 mm, such as about 0.81 mm. Other dimensions are also envisioned depending on the desired clinical result.

Figure 11R:
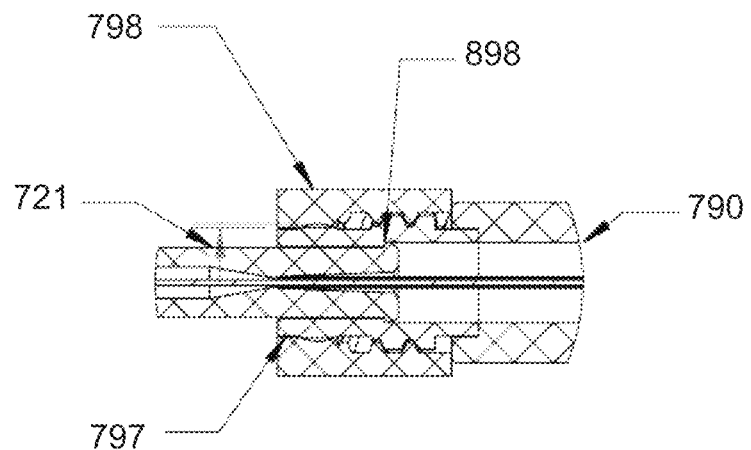
Figure 11S:
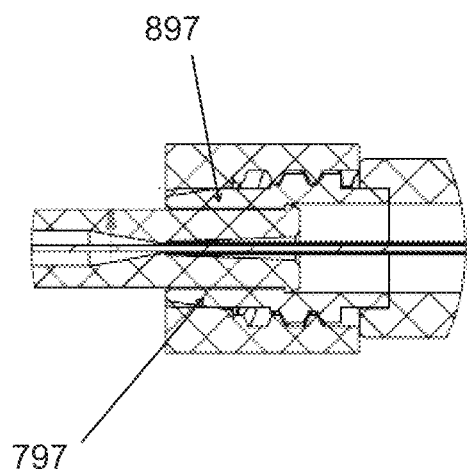

FIGS. 11R and 11S illustrate close-up views of a collet lock and taper lock respectively, according to some embodiments. FIG. 11R illustrates collet nut 798, collet 797, catheter holder 721, and catheter handle 791. A one-way tab 898 in the catheter can be present under a cut section of the collet 797. FIG. 11S illustrates that the collet 797 has a tapered surface 897.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "accessing the inferior orbital fissure" includes "instructing the accessing of the inferior orbital fissure." The ranges disclosed herein also encompass any and all overlap, subranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method of treating a patient, comprising:
   accessing the sphenopalatine fossa; and
   cannulating the inferior orbital fissure from the sphenopalatine fossa to access the retro-orbital space,
   wherein cannulating the inferior orbital fissure comprises inserting a catheter that extends distally from an exit port of a needle positioned in the sphenopalatine fossa through the inferior orbital fissure.

2. The method of claim 1, wherein the sphenopalatine fossa is accessed percutaneously.

3. The method of claim 1, wherein accessing the sphenopalatine fossa comprises inserting the needle into the sphenopalatine fossa.

4. The method of claim 1, wherein accessing the sphenopalatine fossa comprises inserting the needle percutaneously proximate the coronoid process of the mandible; and redirecting the needle to the superior aspect of the sphenopalatine fossa.

5. The method of claim 1, wherein accessing the sphenopalatine fossa comprises inserting the needle percutaneously inferior to the zygomatic arch to contact the lateral pterygoid plate; and redirecting the needle to the superior aspect of the sphenopalatine fossa.

6. The method of claim 1, wherein at least part of the method is performed under fluoroscopy.

7. The method of claim 1, wherein cannulating the inferior orbital fissure comprises inserting the catheter into the medial aspect of the inferior orbital fissure.

8. The method of claim 1, wherein inserting a catheter through the inferior orbital fissure comprises inserting the catheter at an angle to the longitudinal axis of the needle.

9. The method of claim 1, wherein inserting a catheter through the inferior orbital fissure comprises inserting the catheter a distance from about 2 cm to about 4 cm beyond the exit port of the needle.

10. The method of claim 8, wherein the angle is between about 10 degrees and about 20 degrees.

11. The method of claim 1, further comprising locking the catheter to the needle to prevent relative axial movement of the catheter with respect to the needle.

12. The method of claim 11, further comprising unlocking the catheter to the needle to allow relative axial movement of the catheter with respect to the needle.

13. The method of claim 1, further comprising delivering at least one therapeutic agent to the retro-orbital space.

14. The method of claim 13, wherein the therapeutic agent comprises a drug.

15. The method of claim 14, wherein the therapeutic agent comprises a stem cell.

16. The method of claim 1, further comprising electrically stimulating a tissue proximate the retro-orbital space.

17. The method of claim 1, further comprising removing material from the retro-orbital space.

* * * * *